(12) United States Patent
Walker et al.

(10) Patent No.: US 7,790,706 B2
(45) Date of Patent: Sep. 7, 2010

(54) TREATMENT OF INFLAMMATION WITH 5α REDUCED METABOLITES

(75) Inventors: Brian Robert Walker, Edinburgh (GB); Ruth Andrew, Edinburgh (GB)

(73) Assignee: The University of Edinburgh, Edinburgh (GB)

(*) Notice: Subject to any disclaimer, the term of this patent is extended or adjusted under 35 U.S.C. 154(b) by 864 days.

(21) Appl. No.: 11/011,977

(22) Filed: Dec. 14, 2004

(65) Prior Publication Data

US 2005/0130946 A1 Jun. 16, 2005

Related U.S. Application Data

(63) Continuation-in-part of application No. PCT/GB03/02597, filed on Jun. 16, 2003.

(30) Foreign Application Priority Data

Jun. 14, 2002 (GB) .................................. 0213745.3

(51) Int. Cl.
*A61K 31/56* (2006.01)
*A01N 45/00* (2006.01)
(52) U.S. Cl. .................. 514/182; 514/170; 514/178; 514/169
(58) Field of Classification Search .................. None
See application file for complete search history.

(56) References Cited

U.S. PATENT DOCUMENTS

| | | | |
|---|---|---|---|
| 5,358,943 A | 10/1994 | Clark et al. | |
| 5,474,765 A * | 12/1995 | Thorpe | 424/78.17 |
| 5,939,069 A | 8/1999 | Clare-Salzler | |
| 6,809,178 B2 * | 10/2004 | Evans et al. | 530/350 |
| 2001/0021510 A1 | 9/2001 | Clare-Salzer | |
| 2002/0042425 A1 | 4/2002 | Gormley et al. | |
| 2002/0192217 A1 * | 12/2002 | Calandra et al. | 424/145.1 |

FOREIGN PATENT DOCUMENTS

| | | |
|---|---|---|
| CN | 1327827 | 12/2001 |
| JP | 61-106520 | 5/1986 |
| JP | 08-259465 | 10/1996 |
| WO | WO 92/08355 | 5/1992 |
| WO | WO 99/07357 | 2/1999 |
| WO | WO 99/22728 | 5/1999 |
| WO | WO 99/36030 | 7/1999 |
| WO | WO 01/15774 | 3/2001 |
| WO | WO 02/64134 A2 | 2/2002 |
| WO | WO 03/059267 A2 | 7/2003 |
| WO | WO 03/105838 A2 | 12/2003 |

OTHER PUBLICATIONS

Alam et al. 1997. Angiogenesis. 1:185-191.*
Li et al. 1991. Investigative Opthalmology and Visual Sci. 32:2898-2905.*
Colby et al (1975. Endocrinology 96:1153-1157).*
Carolin Lackner, Glucocorticoid-Recognizing And-Effector Sites In Rat Liver Plasma Membrane. Kinetics Of Corticosterone Uptake By Isolated Membrane Vesicles. III. Specificity And Stereospecificity, J. Steroid Biochem. Molec. Biol. (1998) vol. 64, No. 12, p. 69-82.
Gianfranco Altomare and Giovanni Luigi Capella; Depression Circumstantially Related to the Administration of Finasteride for Androgenetic Alopecia; The Journal of Dermatology, vol. 29:665-669, 2002.
Tina S. Berger, Zahra Parandoosh, Bruce W. Perry and Robert B. Stein; Interaction of Glucocorticoid Analogues with the Human Glucocorticoid Receptor; Ligand Pharmaceuticals Inc., Steroid Biochm. Molec. Biol., vol. 41, No. 3-8, pp. 733-738, 1992.
R.E. Brown, MD, W.P. Bowman, MD, C.A. D'Cruz, MD, T.E. Pick, MD; and J.E. Champion, MD; Endoperoxidation, Hyperprostaglandinemia, and Hyperlipidemia in a Case of Erytrophagocytic Lymphohistiocytosis; Cancer, Nov. 15, 1987, vol. 60, pp. 2388-2393.
Jordi Bruix, Jaume Bosch, David Kravetz, Richardo Mastai, Joan Rodes, Effects of Prostaglandin Inhibition on Systemic and Hepatic Hemodynamics in Patients with Cirrhosis of the Liver; Gastroenterology, 1985; 88: 430-5.
W. Chen, Ch. C. Zouboulis, C.E. Orfanos, The 5αReductase System and Its Inhibitors; Dermatology 1996; 193:177-184.
Paul R. Colville-Nash, Chandan A.S. Alam, Ian Appleton, Joanne R. Brown, Michael P. Seed, and Derek A. Willoughby, The Pharmacological Modulation of Angiogenesis in Chronic Granulomatous Inflammation, the Journal of Pharmacology and Experimental Therapeutics, vol. 274, No. 3, pp. 1463-1472.
E.P.M. Corssmit, J.A. Romijn, E. Endert, H.P. Sauerwein; Indomethacin stimulates basal glucose production in humans without changes in concentrations of glucoregulatory hormones; Clinical Science, 1993, 85, pp. 679-685.
B. Dubrovsky, D. Williams, and I Kraulis; Effects of Corticosterone and 5α-Dihydrocorticosterone on Brain Excitability in the Rat, 1985 Alan R. Liss, Inc., Journal of Neuroscience Research 14:117-128 (1985).
Bertil B. Fredholm and Per Hedqvist, Indomethacin and the Role of Prostaglandins in Adipose Tissue; Biochemical Pharmacology, vol. 24, pp. 61-66, 1975.
Akihiko Fuji, Shinichi Kakumu, Yoshiyuki Ohtani, Kenichi Murase, Hideo Hirofuji and Hirofumi Tahara, Interferon-γ Production by Peripheral Blood Mononuclear Cells of Patients with Chronic Liver Disease; Hepatology, vol. 7, No. 3, pp. 577-581, 1987.
S.W. Golf, F. Bepperling and V. Graef; Effect of 5α-Dihydrocorticoids on Enzymes of Gluconeogenesis in Rat Liver; Steroids, vol. 43, No. 1, Jan. 1984.

(Continued)

*Primary Examiner*—Gary B Nickol
*Assistant Examiner*—Shulamith H Shafer
(74) *Attorney, Agent, or Firm*—Frommer Lawrence & Haug LLP; Thomas J. Kowalski; Smitha B. Uthaman

(57) ABSTRACT

The present invention relates to the modulation of glucocorticoid metabolism. In particular the invention relates to the modulation of the functional activity of the glucocorticoid receptor by 5α reduced metabolic breakdown products of glucocorticoids.

6 Claims, 6 Drawing Sheets

OTHER PUBLICATIONS

Usah Lilavivathana and Roberrt G. Brodows; Indomethacin and Aspirin Prevent the Starvation-Induced Fall in Plasma Insulin; Journal of Clinical Endrocrinology and Metabolism, 1980, vol. 50, No. 5, pp. 923-926.

Eric S. Knochenhauer and Ricardo Azziz; Advances in the diagnosis and treatment of the hirsuite patient; Current Opinion in Obstetrics and Gynecology 1995, 7:344-350.

Rusahr G. Kokate, Bjorn E. Svensson and Michael A. Rogawski, Anticonvulsant Activity of Neurosteroids: Correlation with γ-Aminobutyric Acid-Evoked Chloride Current Potentiation; The Journal of Pharmacology and Experimental Therapeutics, 1994, PET 270: 1223-1229, 1994.

Trevor M. Penning, Indomethacin and Glucocorticoid Metabolism in Rat Liver Cytosol; Biochemical Pharmacology, vol. 35, No. 23, pp. 4203-4209, 1986.

Judy A. Spitzer, Inia Hikawj-Yevich, James B. Heneghan; Modulation of Lipolysis by Endotoxin and Indomethacin in Fat Cells of Germfree and Conventional Dogs; Life Sciences, vol. 21, pp. 675-682, 1977.

Beverly A Teicher, Sylvia A. Holden, Gulshan Ara; Timothy Korbut, Krishna Menon; Comparison of several antiangiogenic regimens alone and with cytotoxic therapies in the Lewis lung carcinoma; Cancer Chemother Pharmacol (1996) 38: 169-177, Springer-Verlag 1996.

* cited by examiner

TREATMENT OF INFLAMMATION WITH 5α REDUCED METABOLITES

INCORPORATION BY REFERENCE

This application is a continuation-in-part application of international patent application Serial No. PCT/GB03/02597 filed Jun. 16, 2003, which claims benefit of UK patent application Serial No. GB0213745.3 filed Jun. 14, 2002.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the modulation of glucocorticoid metabolism. In particular the invention relates to the modulation of the functional activity of the glucocorticoid receptor by specific reduced metabolic breakdown products of glucocorticoids.

BACKGROUND OF THE INVENTION

Glucocorticoid hormones have potent anti-inflammatory, cardiovascular and metabolic effects. These include clinically important actions in adipose tissue (promoting obesity, impaired glucose uptake, insulin resistance and hyperlipidaemia), liver (promoting increased glucose production, insulin resistance, and hyperlipidaemia), bone (promoting osteopenia and osteoporosis), the immune system (suppressing inflammatory responses and promoting resolution of inflammation), brain (promoting neurotoxicity, cognitive dysfunction, and mood disturbance), blood vessels (promoting vasoconstriction and hypertension) and kidney (promoting sodium retention and hypertension).

Glucocorticoids are steroids which bind and activate glucocorticoid receptors. Characteristically, these are 21-carbon steroids with 17-hydroxyl, 21-hydroxyl, 11-hydroxyl, 3-keto groups and a double-bond in the 4-5 position. Exemplary glucocorticoids include cortisol (hydrocortisone), dexamethasone, prednisolone, triamcinolone, betamethasone, and beclomethasone.

Glucocorticoid action is mediated largely through activation of glucocorticoid receptors (GR). GR are almost ubiquitously expressed in mammalian cells. Upon binding of glucocorticoid ligand in cytoplasm, these receptors are actively translocated to the nucleus, form heterodimers with other transcription factors and homodimers with each other, and regulate transcription of a wide variety of target genes by binding to GR-response elements in 5' promoter regions. GR activation can stimulate or inhibit gene transcription.

It has been recognised recently that the biological activity of glucocorticoids is influenced in several ways by their peripheral metabolism. Firstly, enzymes metabolising glucocorticoids influence circulating glucocorticoid concentrations and hence control of ACTH and corticosteroid production. Glucocorticoids are inactivated by a series of enzymes, including 6β-hydroxylase, 20-hydroxysteroid dehydrogenase, 5β-reductase, 5α-reductase and 11β-hydroxysteroid dehydrogenases. A-ring reductases (5β-reductase and 5α-reductase) account for the majority of peripheral cortisol metabolism in humans. They convert cortisol to 5β-dihydrocortisol and 5α-dihydrocortisol which are then rapidly converted in liver to 5β-tetrahydrocortisol and 5α-tetrahydrocortisol by 3α-hydroxysteroid dehydrogenase, with the tetrahydro-metabolites then being subject to conjugation by glucuronyl tranferase and sulphonyl transferase enzymes in liver. For exogenous glucocorticoids, activities of these enzymes influences bioavailability. For endogenous glucocorticoids, cortisol and corticosterone, peripheral metabolic clearance rate (determined by the sum of the activities of these metabolising enzymes and by any additional clearance of glucocorticoid in urine or bile) influences circulating glucocorticoid levels and hence influences central feedback control of the hypothalamic-pituitary-adrenal (HPA) axis. Impaired peripheral metabolic clearance results in negative feedback suppression of the HPA axis to maintain normal cortisol levels. Enhanced metabolic clearance results in activation of the HPA axis, which maintains normal cortisol levels in the circulation but at the expense of higher levels of other ACTH-dependent steroids, such as the adrenal androgens dihydroepiandrosterone, androstenedione and their metabolites. This activation of the HPA axis due to enhanced metabolism of cortisol by 5α-reductase has been invoked as a mechanism for androgen excess (and resulting hirsutism and metabolic derangement) in obesity (Andrew et al 1998) and polycystic ovary syndrome (Stewart et al 1990).

Secondly, activity of glucocorticoid metabolising enzymes also influences intracellular glucocorticoid concentrations, and hence modulates activation of corticosteroid receptors within target tissues. This phenomenon is well described for the role of 11β-hydroxysteroid dehydrogenases (11HSDs) (Stewart & Krozowski 1999; Seckl & Walker 2001). 11HSD type 2 is expressed in a limited range of tissues in humans, including distal nephron, colon, and sweat glands. In these sites it inactivates cortisol by converting it to cortisone, an inert steroid, and hence lowers intracellular cortisol concentrations. Failure of this inactivation, for example in congenital 11HSD2 deficiency or after inhibition of 11HSD2 with glycyrrhetinic acid or carbenoxolone, results in increased intracellular cortisol levels (without any change in circulating cortisol levels which are regulated by the HPA axis, as above) and allows cortisol to bind to mineralocorticoid receptors. Normal activity of 11HSD2 prevents significant occupancy of mineralocorticoid receptors by cortisol, and confers on these receptors their selectivity for aldosterone in vivo (Funder et al 1988; Edwards et al 1988). Conversely, 11HSD type 1 is expressed in other tissues, including liver, adipose tissue, the immune system and central nervous system (Seckl & Walker 2001). Here, 11HSD1 reactivates inert cortisone into cortisol, and hence increases intracellular cortisol concentrations. This reaction is important in maintaining activation of glucocorticoid receptors in these tissues (Walker et al 1995; Kotelevtsev et al 1997; Masuzaki et al 2001).

A third mechanism of influence of metabolic enzymes on steroid action has been described for other members of the steroid-thyroid hormone superfamily. This involves conversion of active steroids into metabolites which are themselves biologically active (Stewart & Sheppard 1992). Examples include conversion of thyroxine into tri-iodothyronine by 5'-monodeiodinases, conversion of testosterone into 5α-dihydrotestosterone by 5α-reductases, conversion of oestrone into oestradiol and androstenedione to testosterone by 17β-hydroxysteroid dehydrogenase, and of androstenedione into oestrone by aromatase.

With regard to glucocorticoids, however, metabolites of endogenous glucocorticoid (cortisol in human; corticosterone in rat and mouse) have been reported to be inert, ie without biological activity (Golf et al 1984). With regard to the metabolites produced by 5α-reductase, the subject of this invention, very little experimentation has tested this assumption. Only 5α-dihydrocorticosterone has been examined, with contradictory results. 5α-Dihydrocorticosterone has been reported to oppose glucocorticoid action, eg by lowering activity of gluconeogenic enzymes in liver (Golf et al 1984), but also to mimic glucocorticoid action in inhibition of neuronal long-term potentiation (Dubrovsky et al 1987). These effects have been interpreted as reflecting membrane effects of 5α-dihydrocorticosterone (Dubrovsky et al 1987), a view which is reinforced by the observation that this steroid does not bind to glucocorticoid receptors, as judged by failure to displace bound dexamethasone (Carlstedt-Duke et al 1977).

In clinical use as anti-inflammatory agents (for example in asthma, inflammatory bowel disease, rheumatoid arthritis, polymyalgia rheumatica etc) glucocorticoids induce adverse effects (such as osteoporosis, obesity, insulin resistance, hyperglycaemia, dyslipidaemia, hypertension, mood and sleep disturbance, cognitive dysfunction) because of their actions mediated by glucocorticoid receptors in most tissues. In addition, excess levels of endogenous glucocorticoids may contribute to similar diseases. To prevent these adverse effects of exogenous and endogenous glucocorticoids, while maintaining beneficial anti-inflammatory effects, requires tissue-specific manipulation of glucocorticoid receptor activation. To date, this has been proposed by manipulating reactivation of glucocorticoids within target tissues which express 11HSD1. For other steroids, preventing conversion of the major hormone into an active metabolite also allows tissue-specific manipulation of hormone action, for example in the use of 5α-reductase inhibitors to prevent conversion of testosterone to 5α-dihydrotestosterone in prostate disease or in the use of aromatase inhibitors to prevent conversion of androgens to oestrogens in breast disease. However, no such active metabolite of cortisol or corticosterone is know, so for glucocorticoids this approach has not been proposed.

Thus, there remains a need in the art to identify methods and compositions suitable for modulating the activity of glucocorticoid receptors for therapeutic and other uses.

Citation or identification of any document in this application is not an admission that such document is available as prior art to the present invention.

SUMMARY OF THE INVENTION

The present inventors have surprisingly found that 5α reduced glucocorticoid metabolites but not 5β reduced glucocorticoid metabolites are capable of binding to and activating glucocorticoid receptors. Moreover, the affinity and efficacy of these metabolites for the receptors is greater than the affinity and efficacy of the receptors for their endogenous glucocorticoid ligands. Furthermore, the inventors have shown that modulation of the endogenous levels of 5α reduced metabolites available for receptor binding has no effect on the levels of endogenous glucocorticoid available for receptor binding. Therefore the inventors have demonstrated that by modulating the levels of 5α reduced glucocorticoid metabolites but not 5β metabolites available for glucocorticoid receptor binding, then the activation and subsequent functional effects mediated by glucocorticoid receptor binding can also be modulated.

Thus, in a first aspect the present invention provides a method for modulating the activation of one or more glucocorticoid receptors comprising the step of modulating the functional activity of one or more 5α reduced metabolite/s capable of binding to the one or more receptors.

In a further aspect the present invention provides the use of a modulator of the functional activity of one or more 5α reduced metabolites in the preparation of a medicament for modulating the activation of one or more glucocorticoid receptors.

According to the present invention, the term 'a 5α-reduced metabolite' refers to the one or more products generated as a consequence of the breakdown of endogenous glucocorticoids by 5α-reductase enzymes. Advantageously, the 5α-reduced metabolites of the present invention are selected from the group consisting of the following: 5α-dihydrocorticosterone, 5α-tetrahydrocorticosterone, 5α-dihydrocortisol, and 5α-tetrahydrocortisol. In a most preferred embodiment of this aspect of the invention, the 5α reduced metabolite is 5α-dihydrocorticosterone. Those skilled in the art will be aware of other suitable 5α-reduced metabolites for use according to the invention described herein.

As herein defined, 'a modulator of the functional activity of one or more 5α reduced metabolites' means any agent, method or procedure which results in a change (increase, decrease or otherwise) of the functional activity as herein defined of one or more 5α reduced metabolites. In a preferred embodiment of this aspect of the invention, the modulator is an agent and is selected form the group consisting of finasteride, GI198745, G1108745, LY191704 and indomethacin.

According to the present invention the term 'the functional activity' of one or more 5α reduced metabolites describes the ability of those one or more metabolites to bind to and activate one or more glucocorticoid receptors.

One skilled in the art will appreciate that modulation of a mixture of different 5α reduced metabolites may result in the functional activity of one or a number of reduced metabolites increasing and within the same mixture the functional activity of another one or more metabolites decreasing such that overall the level of receptor binding by the 5α reduced metabolites is the same. In this situation, if the ability of the different reduced metabolites to activate and/or generate glucocorticoid receptor mediated functional effects is not the same in the differing metabolites, then the functional activity of one or more glucocorticoid receptors will be modulated accordingly.

As referred to above the term 'activation of one or more glucocorticoid receptors' refers to the ligand binding and subsequent binding dependent change of form of the one or more receptors such that the one or more receptors are capable of generating one or more 'functional effect/s' as herein defined. Such ligand binding dependent change of form may be brought about by a conformational change in the receptor which occurs on ligand binding. Alternatively, or in addition, the ligand once bound by the receptor may itself provide an effector function which permits the generation of one or more glucocorticoid receptor mediated 'functional effects' as herein defined. Those skilled in the art will be aware of further mechanisms by which ligand binding to one or more receptor/s may facilitate the generation of such 'functional effects'.

According to the present invention, 'modulating the activation of one or more glucocorticoid receptors' includes within its scope increasing or decreasing the number of activated receptors in a sample of one or more receptors which have been brought into binding contact with one or more 5α reduced metabolites as herein defined, when compared with the same or a similar sample of receptors under the same or similar conditions which have not been brought into binding contact with the one or more 5α reduced metabolites as herein defined.

In addition, according to the present invention 'modulating the activation of one or more glucocorticoid receptors' may be mediated by a differing affinity (increased, decreasd or otherwise) of a sample of receptors for one or more 5α reduced metabolites as compared with a sample of the same or similar receptors under the same or similar conditions for the parent glucocorticoid ligand. That is, one or more 5α reduced metabolites as herein described may have an increased or decreased affinity for one or more glucocorticoid receptors as compared with a glucocorticoid ligand bound to the same one or more receptors.

Alternatively or in addition, 'modulating the activation of one or more glucocorticoid receptors' may be achieved by a differing (increase, decreased or otherwise) ability of 5α reduced metabolite bound glucocorticoid receptors as herein defined to generate 'functional effects' as herein described when compared with the same or a similar sample of glucocorticoid receptors under the same or similar conditions which are bound to a glucocorticoid ligand so as to generate functional effects as herein defined.

Those skilled in the art will be aware of other mechanisms by which 5α reduced metabolites may modulate the activation of glucocorticoid receptors as herein defined.

Suitable techniques for modulating glucocorticoid receptor activation will depend upon whether the glucocorticoid receptors to be treated are in vivo or in vitro. Advantageously, glucocorticoid receptor modulation involves a decrease in receptor activation. Suitable in vivo methods for decreasing receptor activation can be selected from the group consisting of the following:

Inhibiting the generation of 5α reduced metabolites by reducing the activity of 5α-reductases. This may be achieved by agents which inhibit 5α-reductase enzyme activity, or reduce levels of 5α-reductase protein.

By reducing the conversion of 5α-dihydrocompounds to 5α-tetrahydro metabolites. This can be achieved for example by agents which inhibit activity of 3α-hydroxysteroid dehydrogenase, or reduce levels of 3α-hydroxysteroid dehydrogenase proteins.

5α-reduced metabolites as herein defined, are actively transported across the cell membrane and into the cytosol (Lackner et al 1998). Inhibition of this transport process reduces access of 5α-reduced steroids to cytosolic nuclear hormone receptors.

By promoting inactivation of glucocorticoids by other routes, for example by 5β-reductase, to lower 5α-reduced metabolite levels. In this regard it is important to note that the present inventors have shown that 5β-reduced glucocorticoid metabolites neither bind nor activate glucocorticoid receptors.

Agents which enhance conjugation of 5α-reduced glucocorticoid metabolites may be employed so that the levels of 5α-reduced metabolites in functional proximity, as herein defined, with the glucocorticoid receptors are reduced as compared with a similar sample of glucocorticoid receptors which have not been treated with the same agent.

In an alternative embodiment of this aspect of the invention the activity of one or more glucocorticoid receptor/s is increased. Activation of one or more receptors may be achieved according to the present invention by bringing one or more 5α-reduced metabolites as herein defined into binding contact with the one or more glucocorticoid receptors. Where the receptor activation is to be performed within an in vivo environment, then advantageously receptor activation may be achieved by administering to the one or more glucocorticoid receptors to be treated a sample (that is more than one molecule|) of one or more 5α reduced glucocorticoid metabolites. Alternatively or in addition, in vivo glucocorticoid receptor/s may be treated with one or more agents which increase the endogenous levels of 5α reduced metabolites. Such agents include but are not limited to A ring reductase enzymes and/or other enzymes or molecules which are involved in the endogenous generation of 5α reduced metabolites. Such agents and/or 5α reduced metabolites and/or the nucleic acid encoding them may be introduced into an in vivo environment using methods known to those skilled in the art including transfection methods, micro-injection, and liposome administration. Those skilled in the art will appreciate that this list is not intended to be exhaustive.

In a further aspect the present invention provides a method for modulating the functional activity of one or more glucocorticoid receptors comprising the step of modulating the functional activity of one or more 5α-reduced metabolite/s capable of binding to the one or more receptors.

In a further aspect the present invention provides the use of a modulator of the functional activity of one or more 5α reduced metabolite/s in the preparation of a medicament for modulating the functional activity of one or more glucocorticoid receptors.

According to the present invention, the term 'modulating the functional activity of a glucocorticoid receptor' means increasing, decreasing or otherwise altering the functional activity of a receptor.

The 'functional activity' of a glucocorticoid receptor refers to the ability of the receptor to produce a functional effect. Likewise the term 'modulating the functional activity of a receptor' refers to a change (increase, decrease or otherwise) of the ability of the receptor to generate functional effects. Generally such a functional effect is achieved by the binding of the specific ligand by its receptor resulting in activation of the receptor. This may be achieved by for example a conformational change occurring within the receptor on ligand binding and which results in the functional activation of the receptor. That is, binding of a specific ligand by the receptor places the receptor in a form such that it generate functional effects. Those skilled in the art will appreciate that the 'functional activity' of a glucocorticoid receptor may vary according to its environment within an organism. That is such a receptor situated within adipose tissue may have a different range of functional effects as the same receptor when situated within a different tissue.

Such functional effects include but are not limited to increasing or decreasing the transcription of glucocorticoid receptor regulated target gene expression and/or modulating the functional activity of other molecules (for example proteins) which are bound by and are regulated by activated glucocorticoid receptors. Those skilled in the art will be aware of other functional effects which may occur subsequent to the binding of a glucocorticoid by its one or more specific receptors.

For the avoidance of any doubt, as referred to above the term 'specific binding' of a ligand by its one or more receptors refers to binding of a ligand/receptor pair in a manner which is, replicates or mimics functional binding of the ligand/receptor pair as occurs in nature and has the potential to discriminate between two or more potential ligand/receptor pairings. Non-specific binding, on the other hand, denotes the general association between ligands and receptors which does not have the potential to result in a functional biological interaction and is generally non-discriminatory. One skilled in the art will appreciate that any given receptor may bind one or more than one ligand specifically. Moreover, any given ligand may be bound by more than one receptor specifically. In addition, the site of binding of two different ligands may be at the same site or at different sites within any given receptor.

According to the present invention the term 'the functional activity' of one or more 5α reduced metabolites describes the ability of those one or more metabolites to bind to and activate one or more glucocorticoid receptors.

Techniques for measuring levels of 5α reduced metabolites as herein defined will be familiar to those skilled in the art. The technique selected will depend upon whether metabolites levels are to be measured in vitro or in vivo. Suitable methods include immunoassay and chromatographic measurements, including thin layer chromatography, high performance liquid chromatography and gas chromatography/mass spectrometry (Andrew et al 1998; Livingstone et al 2000). Those skilled in the art will appreciate that this list is not intended to be exhaustive.

The methods of the present invention may be used to modulate the activation and/or functional activity of glucocorticoid receptors in an vivo or an in vitro environment. Advantageously, the method of the invention is used to modulate the activation and/or activity of glucocorticoid receptors within an in vivo environment.

According to the methods and uses of the present invention, a glucocorticoid receptor may be any one selected from the group consisting of the following: the type 2 corticosteroid receptor (Bamberger et al 1996), the low-affinity glucocorticoid binding site (Lopez-Guerra et al 1997), and the membrane receptor (Lackner et al 1998). Those skilled in the art will appreciate that this list is not intended to be exhaustive.

The inventors have shown that the methods of the invention are particularly advantageous since modulating the levels of 5α-reduced metabolites does not influence the availability of endogenous cortisol for glucocorticoid receptor binding, since compensatory changes in HPA axis activity maintain normal cortisol concentrations.

The methods of the present invention are effective in tissues of an organism where 5α-reductases are expressed, including liver, skin, adipose tissue, brain and prostate (Russell & Wilson 1994) and ovary. Hence they will reduce glucocorticoid effects in these tissues, including in liver (preventing glucocorticoid-dependent promotion of gluconeogenesis, resistance to insulin, intra-hepatic fat accumulation, non-alcoholic steatohepatitis and cirrhosis, and hyperlipidaemia), adipose (preventing glucocorticoid-dependent increase in lipid accumulation, resistance to insulin, and inhibition of glucose uptake), brain (preventing glucocorticoid-associated cognitive decline and mood disturbance) and skin (preventing glucocorticoid-induced skin thinning, bruising, hirsutism, and acne). The interactions between 5α-reductase and 3α-HSD can be exploited in sites where these enzymes are expressed together, including liver, brain and prostate (Jin & Penning 2001; Steckelbroeck et al 2001). Those skilled in the art will appreciate that this list is not intended to be exhaustive.

In addition, the present inventors have found that an additional benefit of lowering the rate of inactivation of cortisol by manipulation of A-ring reductases is reduced adrenal androgen excretion as a result of reduced ACTH stimulation of adrenal cortices. This predicts reduced androgen effects in skin (hirsutism and acne), and on reproductive function (irregular menstrual cycles and anovulatory infertility).

According to the present invention the utility of lowering endogenous 5α-reduced glucocorticoid metabolite concentrations is greater in circumstances in which endogenous 5α-reduced metabolites are present at higher concentration. This occurs when there is increased 5α-reductase metabolism of glucocorticoids, including in idiopathic obesity (Andrew et al 1998), polycystic ovary syndrome (Stewart et al 1990) and essential hypertension (Soro et al 1995; Walker et al 1998) in humans, and when there is increased cortisol production of any cause, including in Cushing's syndrome (Phillipou 1982).

Thus in a further aspect the present invention provides a method for inhibiting one or more glucocorticoid mediated effects in one or more tissues of a patient, those effects being selected from the group consisting of the following: in liver (glucocorticoid-dependent promotion of gluconeogenesis in liver, resistance to insulin in liver, intra-hepatic fat accumulation, non-alcoholic steatohepatitis in liver and cirrhosis of the liver, and hyperlipidaemia), adipose (glucocorticoid-dependent increase in lipid accumulation, resistance to insulin, and inhibition of glucose uptake), brain (glucocorticoid-associated cognitive decline and mood disturbance) and skin (preventing glucocorticoid-induced skin thinning, bruising, hirsutism, and acne) comprising the step of inhibiting the functional activity of one or more 5α reduced metabolite/s capable of binding to one or more glucocorticoid receptors.

In a further aspect the present invention provides the use of one or more inhibitors of the functional activity of one or more 5α reduced metabolite/s in the preparation of a medicament for the prophylaxis or treatment of a condition selected from the group consisting of the following: in liver (glucocorticoid-dependent promotion of gluconeogenesis in liver, resistance to insulin in liver, intra-hepatic fat accumulation, non-alcoholic steatohepatitis in liver and cirrhosis of the liver, and hyperlipidaemia), adipose (glucocorticoid-dependent increase in lipid accumulation, resistance to insulin, and inhibition of glucose uptake), brain (glucocorticoid-associated cognitive decline and mood disturbance) and skin (preventing glucocorticoid-induced skin thinning, bruising, hirsutism, and acne).

In a preferred method or use of the above aspects of the invention the condition or glucocorticoid mediated effect is any selected from the group consisting of the following: obesity, insulin resistance, polycystic ovary syndrome, diabetes mellitus, skin disorders (hirsutism, acne) cognitive impairment and glucocorticoid-associated mood disturbance.

As referred to above, the term 'inhibiting' (a condition or glucocortiocoid mediated effect) includes within its scope the partial inhibition (of a condition or glucocorticoid mediated effect as compared with the same effect or condition which has not been treated according to the methods or uses of the present invention). Preferably the inhibition (of a condition or glucocorticoid mediated effect as compared with the same effect or condition which has not been treated according to the methods or uses of the present invention) is at least 20%, 30%, 40%, 50%, or 60%. More preferably still, it is at least 70%, 80% or 90%. Most preferably, the inhibition (of a condition or glucocorticoid mediated effect as compared with the same effect or condition which has not been treated according to the methods or uses of the present invention) is 100%. In addition, according to the present invention the term 'inhibiting' includes within its scope 'preventing' or 'significantly preventing' the above listed effects as outlined above.

Likewise, 'an inhibitor of the functional activity of one or more 5α reduced metabolites' as herein defined includes any molecule which inhibits as described above (including partial inhibition) and/or prevents as described above the ability of one or more 5α reduced metabolites as herein defined to bind to and activate as herein defined one or more glucocorticoid receptors.

Drugs which inhibit or partially inhibit 5α-reductase activity are known in the art and include finasteride, GI198745 (Hirsch et al 1993; Guarna et al 1998; Bartsch et al 2000) and LY191704.

In addition the term 'an inhibitor of the functional activity of one or more 5α reduced metabolites' as used herein includes within its scope any method or procedure which results in the inhibition or partial of the functional activity of one or more 5α reduced metabolites. Such methods have been outlined previously and include Inhibiting the generation of 5α reduced metabolites by reducing the activity of 5α-reductases. This may be achieved by agents which inhibit 5α-reductase enzyme activity, or reduce levels of 5α-reductase protein.

By reducing the conversion of 5α-dihydrocompounds to 5α-tetrahydro metabolites. This can be achieved for example by agents which inhibit activity of 3α-hydroxysteroid dehydrogenase, or reduce levels of 3α-hydroxysteroid dehydrogenase proteins.

5α-reduced metabolites as herein defined, are actively transported across the cell membrane and into the cytosol (Lackner et al 1998). Inhibition of this transport process reduces access of 5α-reduced steroids to cytosolic nuclear hormone receptors.

By promoting inactivation of glucocorticoids by other routes, for example by 5β-reductase, to lower 5α-reduced metabolite levels. In this regard it is important to note that the present inventors have shown that 5β-reduced glucocorticoid metabolites neither bind nor activate glucocorticoid receptors.

Agents which enhance conjugation of 5α-reduced glucocorticoid metabolites may be employed so that the levels of 5α reduced metabolites in functional proximity, as herein defined, with the glucocorticoid receptors are reduced as compared with a similar sample of glucocorticoid receptors which have not been treated with the same agent.

Preferably the methods of the present invention are performed in an in vivo environment. Advantageously, the in vivo environment is a human being.

The inventors have additionally surprisingly found that decreasing the activity of 5α reductase (an A-ring reductase) results in reduced adrenal androgen excretion as a result of reduced ACTH stimulation of adrenal cortices.

Thus in a further aspect the present invention provides a method for preventing and/or treating a condition selected from the group consisting of the following: hirsutism and acne, balding, irregular menstrual cycles and anovulatory infertility comprising the step of inhibiting the functional activity of one or more 5α reduced metabolite/s capable of binding to the one or more receptors.

Preferably the methods of the present invention are performed in an in vivo environment. Advantageously, the in vivo environment is a human being.

In addition, the studies of the present inventors indicate that medicinal administration of 5α-reduced glucocorticoid metabolites will have glucocorticoid action, which is useful in the prophylaxis or treatment of inflammatory conditions. The advantage over administration of the 'parent' compound (ie the 5α-oxidised conventional glucocorticoid hormone) is that 5α-reduced steroids are rapidly conjugated to glucuronides and sulphates in the liver and hence are cleared very rapidly from the systemic circulation. The conjugates are inert and rapidly excreted in urine. In this regard it should be noted that no known pathway exists to convert 5α-reduced glucocorticoids into their 'parent' glucocorticoid hormone. Thus, administration of 5α-reduced glucocorticoid metabolites to skin (for example by topical administration), lung (by for example by inhalation), colon (for example by suppository or enema), joints (for example by intra-articular injection), or liver (for example by mouth, with highly effective first pass conjugation preventing access to the systemic circulation) will target glucocorticoid action to the desired tissue while limiting or preventing systemic glucocorticoid side effects.

Such glucocorticoid mediated side effects include suppression of the HPA axis, osteopenia and osteoporosis, immunocompromise, mood disturbance and insomnia, and adverse metabolic (hyperglycaemia, hyperlipidaemia, obesity) and cardiovascular (hypertension, fluid retention) effects.

Thus in a further aspect the present invention provides a composition comprising one or more 5α reduced metabolite/s and a physiologically acceptable carrier diluent or exipient.

In a further aspect still the present invention provides a method for the treatment of one or more inflammatory conditions in a patient comprising the step of increasing the functional activity of one or more 5α reduced metabolite/s in the one or more sites of inflammation of a patient.

In yet a further aspect the present invention provides, the use of one or more activator/s of the functional activity of one or more 5α reduced metabolite/s in the preparation of a medicament for the prophylaxis or treatment of one or more inflammatory conditions in a patient.

As herein described an 'activator of the functional activity of one or more 5α reduced metabolites' includes any molecule or procedure which increases the ability of one or more 5α reduced metabolites as herein defined to bind to and activate as herein defined one or more glucocorticoid receptor/s.

According to the above aspects of the invention, advantageously, the functional activity of one or more 5α reduced glucocorticoid metabolites is increased by any of the procedures selected from the group consisting of: administering to a patient in need of such treatment a therapeutically effective amount of one or more 5α reduced metabolite/s, increasing 5α reductase activity, reducing pathways of inactivation of cortisol, reducing the conjugation of 5α reduced metabolites and effecting the conversion of 5α-dihydro reduced metabolite compounds to the more active 5α-tetrahydro reduced metabolite compounds. Most advantageously, the functional activity of one or more 5α reduced glucocorticoid metabolites is increased by administering to a patient in need of such treatment a therapeutically effective amount of one or more 5α reduced metabolite/s.

According to the above aspects of the invention, preferably the 5α reduced metabolites are one or more selected from the group consisting of the following: 5α-dihydrocortisol, 5α-tetrahydrocortisol, 5α-dihydrocorticosterone and 5α-tetrahydrocorticosterone.

A particular advantage in the treatment of inflammatory or other conditions by activation of endogenous glucocorticoid receptors using 5α-reduced metabolites is that such receptors are ubiquitously expressed throughout tissues, so that their activation in tissues where receptors are not normally activated can be effected. Those skilled in the art will be aware of suitable routes of administration of 5α reduced metabolites, agents which effect their metabolism and/or the nucleic acid encoding them to tissues. Examples are also given in the detailed description of the invention.

The present inventors have also surprisingly found that 5αreduced metabolites inhibit angiogenesis. Specifically, they have found that angiogenesis in developed vascular tissue (aortic ring tissue) is inhibited by 5alpha-tetrahydrocorticosterone. Details are given in Example 8.

Thus in a further aspect the present invention provides a method for modulating angiogenesis within a population of cells comprising the step of modulating the functional activity of one or more 5α-reduced metabolites according to the invention within that population of cells.

In a further aspect still the invention provides the use of one or more modulators of the functional activity of one or more 5α-reduced metabolites in the preparation of a medicament for modulating angiogenesis within a population of cells.

As used herein, the term 'angiogenesis' refers to the formation of blood vessels from surrounding cells. This may occur during for example tissue repair, during wound healing, in the uterine endometrium, during ischaemia (eg in diabetic retinopathy), in the vessel wall in response to intraluminal injury, in the ovarian follicle, and/or during the invasive growth of tumours. According to the above aspect of the invention, the term 'modulation of angiogenesis' refers to either increasing or decreasing the number of vessels generated during the angiogenesis process as compared with the number of vessels produced in suitable controls. The term the 'modulation of angiogenesis' as defined herein also includes within its scope any alteration in the pattern of vessel formation in the presence of an angiogenesis modulating agent or procedure as herein described. Advantageously the 'modulation of angiogenesis' according to the above aspects of the invention is an inhibition of angiogenesis. Most advantageously as described herein the modulation of angiogenesis is achieved by the use of a modulating agent.

Suitable modulators of the functional activity of 5α-reduced metabolites are described herein, in particular in the detailed description of the invention. Modulators of the functional activity, as herein defined of one or more 5αreduced metabolites as defined herein may activate the functional activity or inhibit the functional activity of the one or more 5αreduced metabolites. In a preferred embodiment of the above aspects of the invention the one or more modulators of the functional activity of the one or more 5α-reduced metabolites are activators of the functional activity of the one or more 5α-reduced metabolites and the modulation of angiogenesis as defined herein involves the inhibition of angiogenesis.

According to the present invention, the modulation of angiogenesis using modulators of the functional activity of one or more 5α-reduced metabolites according to the invention may occur in vivo or in vitro. In a preferred embodiment of the above aspects of the invention the modulation occurs in vivo.

The present inventors consider that the modulation of angiogenesis using 5α-reduced metabolites according to the present invention will find use in the prophylaxis and/or treatment of many and varied conditions including any of those selected from the group consisting of: wound healing, vascular restenosis after injury, cancer and tumour growth, collateral circulation after ischaemia or infarction, stroke, diabetic retinopathy, haemangiomas, follicular rupture in ovaries, and endometrial hyperplasia with or without menorrhagia. Those skilled in the art will appreciate that this list is not intended to be exhaustive.

According to the invention described herein the tissue specificity of action of the one or more 5α-reduced metabolites and/or the compositions comprising them may be achieved by their tissue specific administration. Alternatively, or in addition the tissue specificity of action of the metabolites may be achieved by selective conversion of the less potent 5α-dihydro compounds to the more active 5α-tetrahydrocompounds. This may be achieved for example by design of ligands which are substrates for one of the isozymes of 3α-HSD (Jin & Penning 2001). These isozymes have different tissue distribution and thus activation of 5α-tetrahydrometabolites may be achieved in a tissue specific manner, limiting side-effects.

Further, the invention allows for introduction of 5α-reductase into sites where it is not normally expressed in order to produce local 5α-reduced glucocorticoid metabolites, and thereby have local anti-inflammatory or other effects. This may be desirable, for example using gene therapy in any inflamed tissue, or delivering enzyme within liposomes to macrophages.

The studies reported herein indicate that increasing concentrations of endogenous 5α-reduced metabolites is desirable in order to enhance endogenous glucocorticoid action in liver, adipose, prostate or skin when inflammatory conditions affect these tissues. However, one skilled in the art will appreciate that as described previously, the methods and compositions of the present invention will find use in the treatment of inflammation in many tissues of an organism including those in which 5α reduced glucocorticoid metabolites are not normally expressed.

Preferably, the treatment of one or more inflammatory conditions is performed in a human.

Advantageously, the one or more 5α reduced glucocorticoid metabolites are selected from the group consisting of the following: 5α-dihydrocortisol, 5α-tetrahydrocortisol, 5α-dihydrocorticosterone and 5α-tetrahydrocorticosterone. Most advantageously, at least one of the 5α reduced metabolites is 5α-tetrahydrocorticosterone.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

Dose response. Fold induction of luciferase activity as a consequence of GR activation in Hela cells transfected with GR and luciferase under the control of a GRE and MMTV promoter (n=3). Both steroids activate a glucocorticoid receptor-dependent response. Statistical analysis by Repeated measure ANOVA shows a significant difference ($p<0.05$) in the potency of the two steroids to activate GR, with 5α-tetrahydrocorticosterone (5α-THB) having a lesser effect than corticosterone (B).

Figure 4:
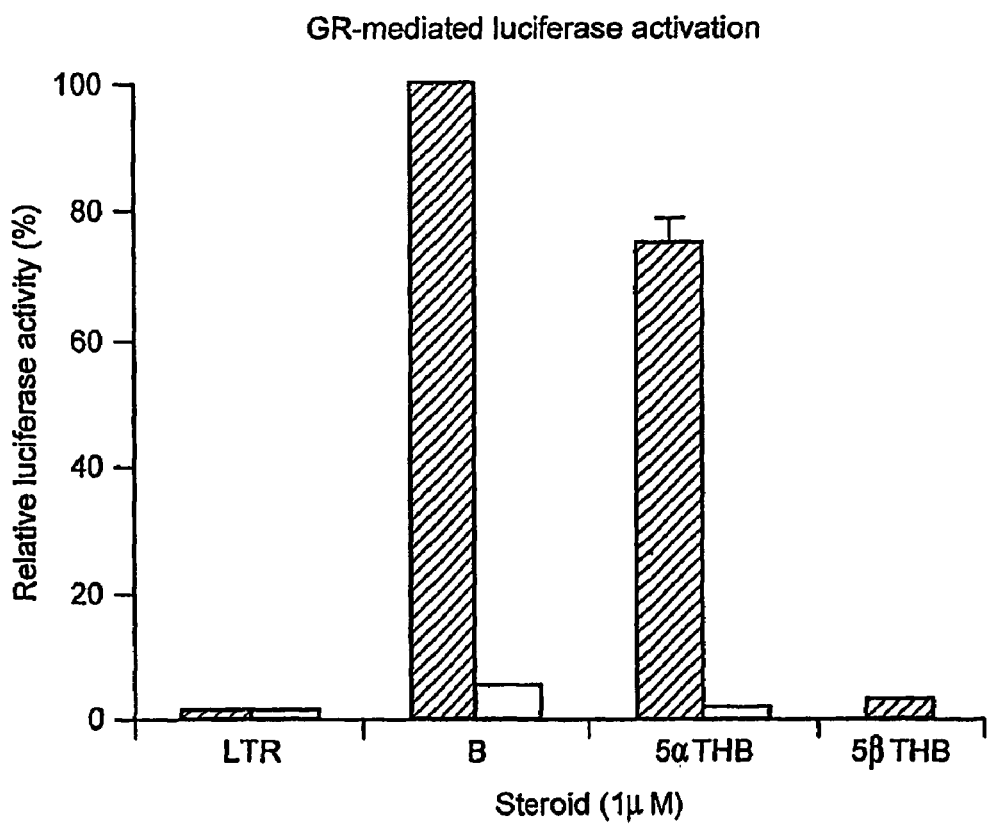

FIG. 4 shows the dependence of reporter gene induction by 5alpha-reduced glucocorticoid metabolites on the presence of the glucocorticoid receptor.

Figure 5:
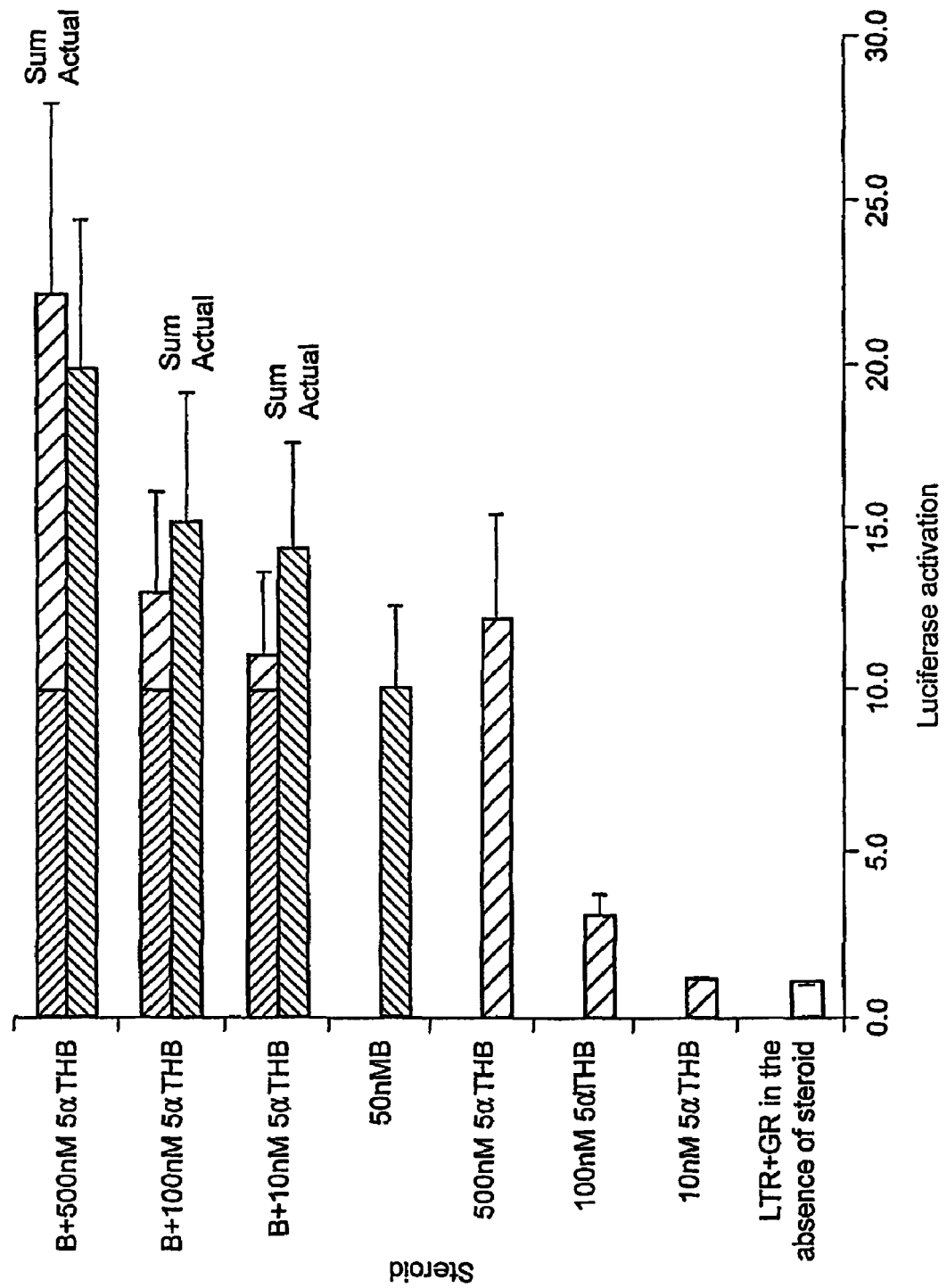

FIG. 5 shows the full agonist rather than partial agonist activity of 5alpha-tetrahydrocorticosterone on glucocorticoid receptors.

Figure 6:
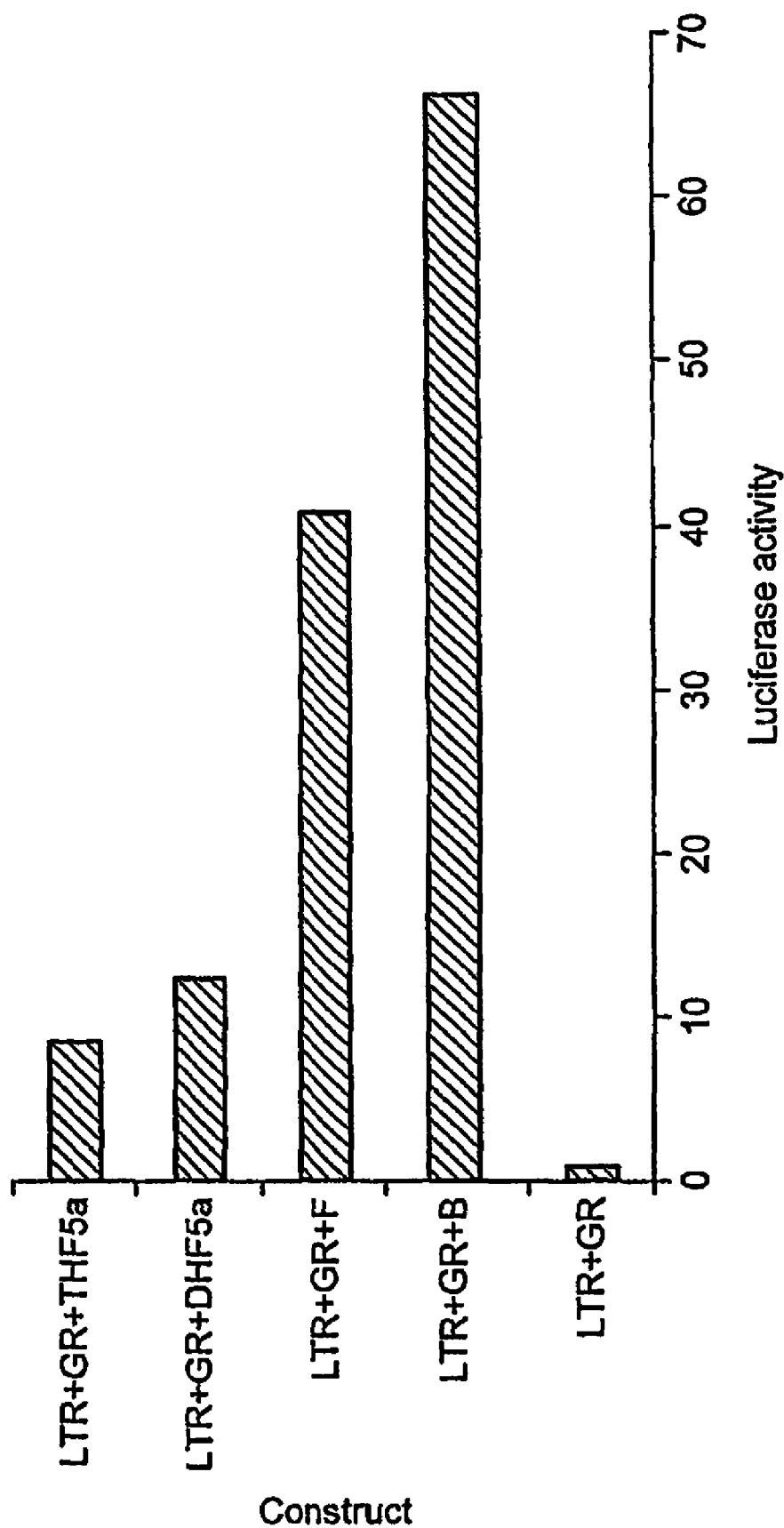

FIG. 6 shows that 5alpha-reduced metabolites of the human glucocorticoid, cortisol, also activate glucocorticoid receptors.

Figure 7:
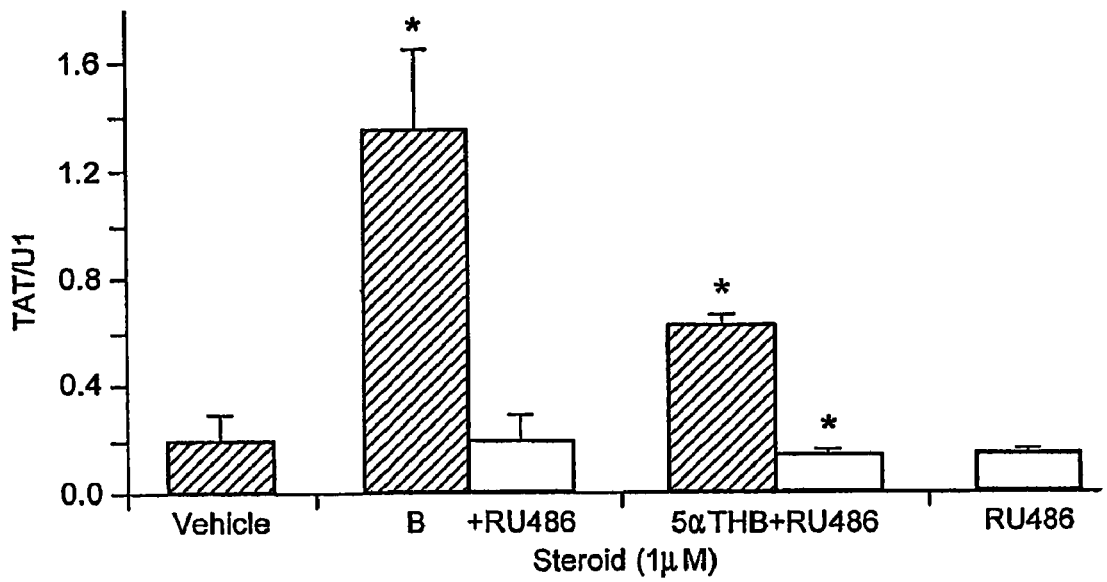

FIG. 7 shows that 5alpha-reduced glucocorticoid metabolites are glucocorticoid receptor (GR) agonists in cells which express endogenous glucocorticoid receptors.

Figure 8:
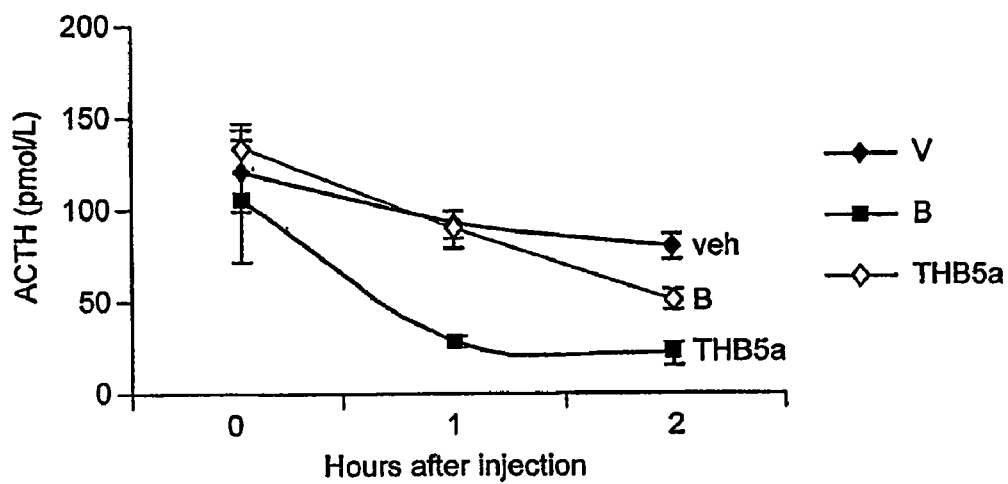

FIG. 8 shows that 5alpha-tetrahydrocorticosterone is a glucocorticoid receptor agonist in vivo.

Figure 9:
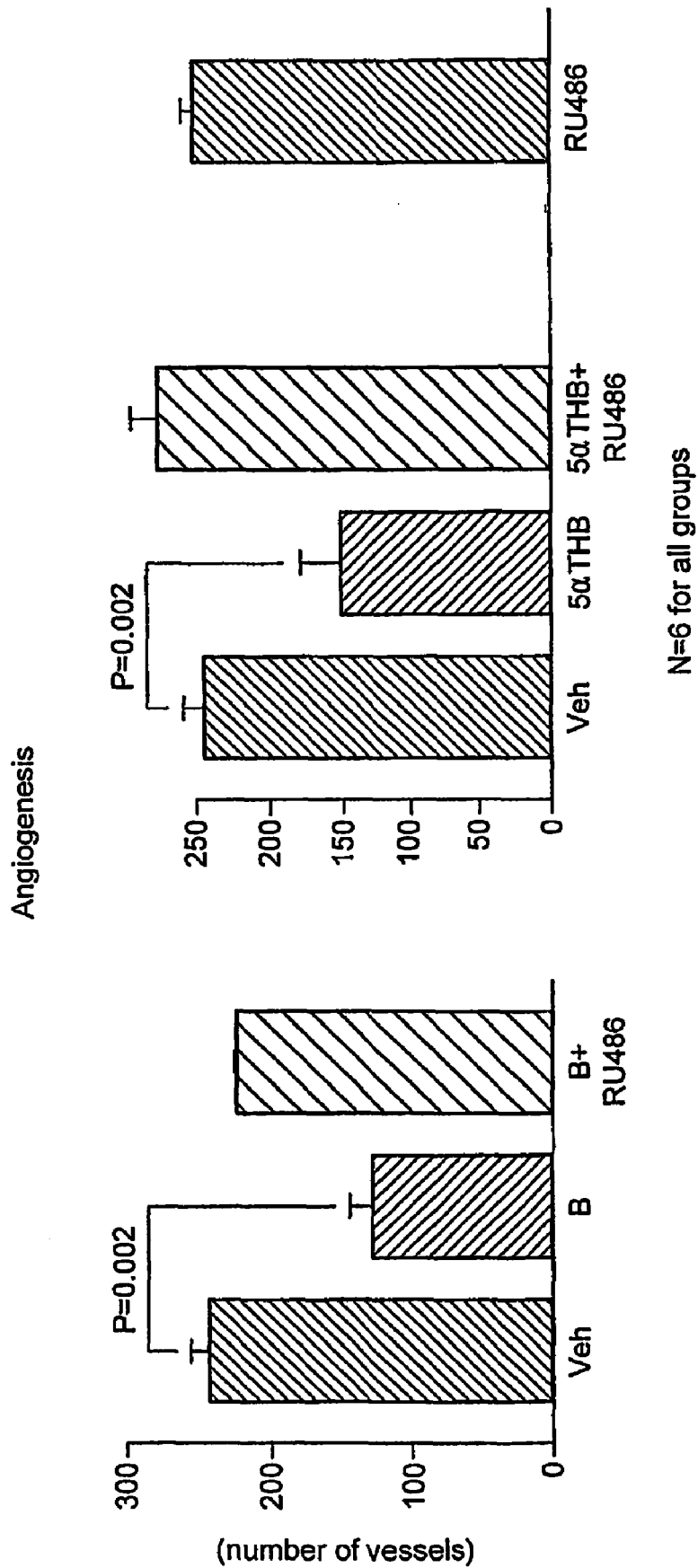

FIG. 9 shows that 5alpha reduced metabolites are inhibitors of angiogenesis. Specifically it shows that 5alpha-tetrahydrocorticosterone is a glucocorticoid receptor agonist in intact isolated tissue preparations.

DETAILED DESCRIPTION

The term 'activation of one or more glucocorticoid receptors' refers to the ligand binding and subsequent binding dependent change of form of the one or more receptors such that the one or more receptors are capable of generating one or more 'functional effect/s' as herein defined. Such ligand binding dependent change of form may be brought about by a conformational change in the receptor which occurs on ligand binding. Alternatively, or in addition, the ligand once bound by the receptor may itself provide an effector function.

According to the present invention, 'modulating the activation of one or more glucocorticoid receptors' includes within its scope increasing or decreasing the number of activated receptors in a sample of one or more receptors which have been brought into binding contact with one or more 5α reduced metabolites as herein defined, when compared with the same or a similar sample of receptors under the same or similar conditions which have not been brought into binding contact with the one or more 5α reduced metabolites as herein defined.

In addition, according to the present invention 'modulating the activation of one or more glucocorticoid receptors' may be mediated by a differing affinity (increased, decreasd or otherwise) of a sample of receptors for one or more 5α reduced metabolites as compared with a sample of the same or similar receptors under the same or similar conditions for the parent glucocorticoid ligand. That is, one or more 5α reduced metabolites as herein described may have an increased or decreased affinity for one or more glucocorticoid receptors as compared with a glucocorticoid ligand bound to the same one or more receptors.

Alternatively or in addition, 'modulating the activation of one or more glucocorticoid receptors' may be achieved by a differing (increase, decreased or otherwise) ability of 5α reduced metabolite bound glucocorticoid receptors as herein defined to generate 'functional effects' as herein described when compared with the same or a similar sample of glucocorticoid receptors under the same or similar conditions which are bound to a glucocorticoid ligand so as to generate functional effects as herein defined Glucocorticoid receptor mediated 'functional effects' include but are not limited to increasing or decreasing the transcription of glucocorticoid receptor regulated target gene expression and/or modulating the functional activity of other molecules (for example proteins) which are bound by and are regulated by activated glucocorticoid receptors.

The term 'a 5α reduced metabolite' refers to the one or more products generated as a consequence of the breakdown of endogenous glucocorticoids by 5α-reductase enzymes. Advantageously, the 5α-reduced metabolites of the present invention are selected from the group consisting of the following: 5α-dihydroxycorticosterone, 5α-tetrahydocorticosterone, 5α-dihydrocortisol and 5α-tetrahydocortisol.

The term 'a modulator of the functional activity of one or more 5α reduced metabolites' means any agent, method or procedure which results a change (increase, decrease or otherwise) of the functional activity of one or more 5α reduced metabolites as herein defined.

The term 'inhibiting' (a condition or glucocortiocoid mediated effect) includes within its scope the partial inhibition (of a condition or glucocorticoid mediated effect as compared with the same effect or condition which has not been treated according to the methods or uses of the present invention). Preferably the inhibition (of a condition or glucocorticoid mediated effect as compared with the same effect or condition which has not been treated according to the methods or uses of the present invention) is at least 20%, 30%, 40%, 50%, or 60%. More preferably still, it is at least 70%, 80% or 90%. Most preferably, the inhibition (of a condition or glucocorticoid mediated effect as compared with the same effect or condition which has not been treated according to the methods or uses of the present invention) is 100%. In addition, according to the present invention the term 'inhibiting' includes within its scope 'preventing' or 'significantly preventing' the above listed effects as outlined above.

Likewise, 'an inhibitor of the functional activity of one or more 5α reduced metabolites' as herein defined includes any molecule which inhibits as described above (including partial inhibition) and/or prevents as described above the ability of one or more 5α reduced metabolites as herein defined to bind to and activate as herein defined one or more glucocorticoid receptors.

An 'activator of the functional activity of one or more 5α reduced metabolies' as herein described includes any molecule or procedure which increases the ability of one or more 5α reduced metabolites as herein defined to bind to and activate as herein defined one or more glucocorticoid receptor/s.

As used herein, the term 'angiogenesis' refers to the formation of blood vessels from surrounding cells. This may occur during for example tissue repair and/or during the invasive growth of tumours. According to the above aspect of the invention, the term 'modulation of angiogenesis' refers to either increasing or decreasing the number of vessels generated during the angiogenesis process as compared with the number of vessels produced in suitable controls. The term the 'modulation of angiogenesis' as defined herein also includes within its scope any alteration in the pattern of vessel formation in the presence of an angiogenesis modulating agent or procedure as herein described. Advantageously the 'modulation of angiogenesis' according to the above aspects of the invention is an inhibition of angiogenesis. Most advantageously as described herein the modulation of angiogenesis is achieved by the use of a modulating agent.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods. In addition Harlow & Lane., A Laboratory Manual Cold Spring Harbor, N.Y., is referred to for standard Immunological Techniques.

5α reduced metabolites as referred to herein include but are not limited to any of the following: 5α-dihydrocortisol, 5α-tetrahydrocortisol, 5α-dihydrocorticosterone and 5α-tetrahydrocorticosterone.

In vitro preparation of the metabolites may be performed by the breakdown of 5α-oxidised glucocorticoid hormone. Methods for the isolation and/or preparation of these steroids will be familiar to those skilled in the art.

As described herein in the summary of the invention, the functional activity of 5α reduced metabolites as herein defined may be modulated by a number of methods. The method of modulation will depend upon whether the modulation of reduced metabolite levels is to be performed in vivo or in vitro. In the case where the modulation of reduced metabolite levels is to be performed in vivo, then the following techniques may be employed: administration to one or more tissues to be modulated of 5α reduced metabolites, administration to one or more tissues to be modulated of one or more small molecule or protein based agents which modulate the activity of one or more 5α reduced metabolites and/or modulate the expression of one or more enzymes and/or proteins involved in 5α reduced metabolite metabolism, modulation of the gene expression of suitable enzymes and/or proteins involved in 5α reduced metabolite metabolism (for example inhibiting the gene expression of 5α reductase enzymes, inhibiting the gene expression of 3α-hydroxysteroid dehydrogenase).

Small molecule agents may be synthetic or naturally occurring and include finasteride, GI198745 (Hirsch et al, 1993; Guarna et al 1998; Bartsch et al 2000) indomethacin (Hu et al 2000; Kleinwachter et al 2001; Jin & Penning, 2001) and LY191704 (Hirsch et al).

Alternative small molecule agents may be selected from libraries of such agents by conventional screening technologies, including combinatorial chemical approaches. In an advantageous embodiment, cell-based assays which monitor the biological activity of glucocorticoid receptors may be employed to provide a test system for the screening assay. Luminescent or other read-outs may be used, including in high-throughput applications.

Agents may be protein based or nucleic acid based. Protein and nucleic acid, especially RNA, aptamers may be selected to bind to any desired receptor by techniques such as SELEX. SELEX is a method for the in vitro evolution of nucleic acid molecules with highly specific binding to target molecules. It is described, for example, in U.S. Pat. Nos. 5,654,151, 5,503, 978, 5,567,588 and 5,270,163, as well as PCT publication WO 96/38579, each of which is specifically incorporated herein by reference.

The SELEX method involves selection of nucleic acid aptamers, single-stranded nucleic acids capable of binding to a desired target, from a library of oligonucleotides. Starting from a library of nucleic acids, preferably comprising a segment of randomised sequence, the SELEX method includes steps of contacting the library with the target under conditions favourable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched library of nucleic acids, then reiterating the steps of binding, partitioning, dissociating and amplifying through as many cycles as desired to yield highly specific, high affinity nucleic acid ligands to the target molecule.

SELEX is based on the principle that within a nucleic acid library containing a large number of possible sequences and structures there is a wide range of binding affinities for a given target. A nucleic acid library comprising, for example a 20 nucleotide randomised segment can have $4^{20}$ structural possibilities. Those which have the higher affinity constants for the target are considered to be most likely to bind. The process of partitioning, dissociation and amplification generates a second nucleic acid library, enriched for the higher binding affinity candidates. Additional rounds of selection progressively favour the best ligands until the resulting library is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The iterative selection/amplification method is sensitive enough to allow isolation of a single sequence variant in a library containing at least $10^{14}$ sequences. The method could, in principle, be used to sample as many as about $10^{18}$ different nucleic acid species. The nucleic acids of the library preferably include a randomised sequence portion as well as conserved sequences necessary for efficient amplification. Nucleic acid sequence variants can be produced in a number of ways including synthesis of randomised nucleic acid sequences and size selection from randomly cleaved cellular nucleic acids. The variable sequence portion may contain fully or partially random sequence; it may also contain subportions of conserved sequence incorporated with randomised sequence. Sequence variation in test nucleic acids can be introduced or increased by mutagenesis before or during the selection/amplification iterations and by specific modification of cloned aptamers.

Protein based agents moreover include antibodies raised against any one or more 5α reduced metabolite/s and/or one or more molecules involved in 5α reduced metabolite metabolism (for example 5α reductase enzymes, 3α-hydroxysteroid dehydrogenase). Those skilled in the art will appreciate that this list is not intended to be exhaustive.

Antibodies, as used herein, refers to complete antibodies or antibody fragments capable of binding to a selected target, and including Fv, ScFv, Fab' and F(ab')$_2$, monclonal and polyclonal antibodies, engineered antibodies including chimeric, CDR-grafted and humanised antibodies, and artificially selected antibodies produced using phage display or alternative techniques. Small fragments, such Fv and ScFv, possess advantageous properties for diagnostic and therapeutic applications on account of their small size and consequent superior tissue distribution.

The antibodies according to the invention are especially indicated for diagnostic and therapeutic applications. Accordingly, they may be altered antibodies comprising an effector protein such as a toxin or a label. Especially preferred are labels which allow the imaging of the distribution of the antibody in vivo. Such labels may be radioactive labels or radioopaque labels, such as metal particles, which are readily visualisable within the body of a patient. Moreover, the may be fluorescent labels or other labels which are visualisable on tissue samples removed from patients.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent 0 239 400 (Winter)] and, optionally, framework modification [European Patent 0 239 400; reviewed in international patent application WO 90/07861 (Protein Design Labs)].

Antibodies according to the invention may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired antigen by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with an 11β-HSD1 molecule or with Protein-A.

The invention also provides intracellular antibodies, capable of operating within a cell, for the modulation of the functional activity of 5α reduced glucocorticoid metabolites intracellularly. Intracellular antibodies are advantageously scFv antibodies, expressed intracellularly from expression vectors as is known in the art.

Intracellular antibodies or intrabodies have been demonstrated to function in antigen recognition in the cells of higher organisms (reviewed in Cattaneo, A. & Biocca, S. (1997) *Intracellular Antibodies: Development and Applications*. Landes and Springer-Verlag). This interaction can influence the function of cellular proteins which have been successfully inhibited in the cytoplasm, the nucleus or in the secretory pathway. This efficacy has been demonstrated for viral resistance in plant biotechnology (Tavladoraki, P., et al. (1993) *Nature* 366: 469-472) and several applications have been reported of intracellular antibodies binding to HIV viral proteins (Mhashilkar, A. M., et al. (1995) *EMBO J* 14: 1542-51; Duan, L. & Pomerantz, R. J. (1994) *Nucleic Acids Res* 22: 5433-8; Maciejewski, J. P., et al. (1995) *Nat Med* 1: 667-73; Levy-Mintz, P., et al. (1996) *J. Virol.* 70: 8821-8832) and to oncogene products (Biocca, S., Pierandrei-Amaldi, P. & Cattaneo, A. (1993) *Biochem Biophys Res Commun* 197: 422-7; Biocca, S., Pierandrei-Amaldi, P., Campioni, N. & Cattaneo, A. (1994) *Biotechnology (NY)* 12: 396-9; Cochet, O., et al. (1998) *Cancer Res* 58: 1170-6).

The modulation of gene expression is known to those skilled in the art to be achievable in a number of ways in vivo and in vitro. Antisense techniques as well as direct gene manipulation are known for use in modulating gene expression. The invention thus includes the use of antisense nucleic acids, which may incorporate natural or modified nucleotides, or both, ribozymes, including hammerhead ribozymes, gene knockout such as by homologous recombination, and other techniques for reducing gene expression levels.

Nucleic acid agents may be produced and expressed according to techniques known in the art. Nucleic acids encoding desired agents can be incorporated into vectors for manipulation and expression. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast or mammalian cells even though it is not capable of replicating independently of the host cell chromosome. DNA may also be replicated by insertion into the host genome.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Suitable selectable markers for mammalian cells are those that enable the identification of cells which have been transformed with the nucleic acid in question, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA.

Expression and cloning vectors usually contain a promoter that is recognised by the host organism and is operably linked to the desired nucleic acid. Such a promoter may be inducible or constitutive. The promoters may be operably linked to the nucleic acid in question by removing the promoter from the source DNA, for example by restriction enzyme digestion, and inserting the isolated promoter sequence into the vector. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them into vectors as required, using linkers or adaptors to supply any required restriction sites. Promoters for use in bacterial systems will also generally contain a Shine-Delgarno sequence.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (73). In the E. coli BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other vectors include vectors containing the lambda PL promoter such as PLEX (Invitrogen, NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or PMAL (new England Biolabs, Mass., USA).

Suitable promoting sequences for use with yeast hosts may be regulated or constitutive and are preferably derived from a highly expressed yeast gene, especially a Saccharomyces cerevisiae gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the S. cerevisiae GAL 4 gene, the S. pombe nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter.

Transcription of nucleic acids by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the vector at a position 5' or 3' to the coding sequence, but is preferably located at a site 5' from the promoter.

Advantageously, a eukaryotic expression vector may comprise a locus control region (LCR). LCRs are capable of directing high-level integration site independent expression of transgenes integrated into host cell chromatin, which is of importance especially where the gene is to be expressed in the context of a permanently-transfected eukaryotic cell line in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA.

An expression vector includes any vector capable of expressing nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

Vectors as described above may be used in gene therapy techniques and applied to the treatment of diseases. For example, a nucleic acid sequence encoding an antisense molecule according to the present invention may be inserted into a viral or non-viral vector designed for the delivery of nucleic acids to the cells of a patient, either ex-vivo or in vivo.

Examples of viral vectors include adenovirus vectors, adenoassociated virus vectors, retroviral vectors. Examples of non-viral vectors include naked DNA, condensed DNA particles, liposome-type vectors which may include a targeting moiety and, if applicable, escape peptides derived from viruses, and DNA complexed to targeting moieties such as antibodies or cell surface ligands, which are preferably internalised by the target cell.

Other methods for reducing the functional activity of one or more 5α reduced glucocorticoid metabolites include but are not limited to the following:

Inhibiting the generation of 5α reduced metabolites by reducing the activity of 5α-reductases. This may be achieved by agents which inhibit 5α-reductase enzyme activity, or reduce levels of 5α-reductase protein.

By reducing the conversion of 5α-dihydrocompounds to 5α-tetrahydro metabolites. This can be achieved for example by agents which inhibit activity of 3α-hydroxysteroid dehydrogenase, or reduce levels of 3α-hydroxysteroid dehydrogenase proteins.

5α-reduced metabolites as herein defined, are actively transported across the cell membrane and into the cytosol (Lackner et al 1998). Inhibition of this transport process reduces access of 5α-reduced steroids to cytosolic nuclear hormone receptors.

By promoting inactivation of glucocorticoids by other routes, for example by 5β-reductase, to lower 5α-reduced metabolite levels. In this regard it is important to note that the present inventors have shown that 5β-reduced glucocorticoid metabolites neither bind nor activate glucocorticoid receptors.

Agents which enhance conjugation of 5α-reduced glucocorticoid metabolites may be employed so that the levels of 5α reduced metabolites capable of binding to the glucocorticoid receptors are reduced as compared with a similar sample of glucocorticoid receptors which have not been treated with the same agent.

Suitable techniques for increasing the functional activity of 5α reduced metabolites are detailed in the summary of the invention.

Agents according to the invention may be delivered by conventional medicinal approaches, in the form of a pharmaceutical composition. A pharmaceutical composition according to the invention is a composition of matter comprising at least a one or more 5α reduced metabolites or a modulator of the functional activity of one or more 5α reduced metabolites as an active ingredient. The active ingredient(s) of a pharmaceutical composition according to the invention is contemplated to exhibit excellent therapeutic activity, for example, in the alleviation of cardiovascular diseases. Dosage regima may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

In order to administer the combination by other than parenteral administration, it will be coated by, or administered with, a material to prevent its inactivation. For example, the combination may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the combination of polypeptides is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

Glucocorticoids are a group of adrenocortical steroid hormones whose metabolic effects include stimulation of gluconeogenesis, increased catabolism of proteins, and mobilisation of free fatty acids; they are also known to be potent inhibitors of the inflammatory response (allergic response). The vast majority of glucocorticoid activity in most mammals is from cortisol, also known as hydrocortisone. Corticosterone is the major glucocorticoid in rodents and is also present in humans at about 10% of the concentration of cortisol in plasma. Synthetic glucocorticoids are also known, such as dexamethasone. Cortisol binds to the glucocorticoid receptor in the cytoplasm and the hormone-receptor complex is then translocated into the nucleus, where it binds to its DNA response elements and modulates transcription of relevant genes.

Glucocorticoid receptors are universally present and as a consequence, these steroid hormones have a huge number of effects on physiological systems. The best known and studied effects of glucocorticoids are on carbohydrate metabolism and immune function. Indeed, the name glucocorticoid derives from early observations that these hormones were involved in glucose metabolism. In the fasting state, cortisol stimulates several processes that collectively serve to increase and maintain normal concentrations of glucose in blood.

Glucocorticoids are known to have potent anti-inflammatory and immunosuppressive properties. This is particularly evident when they administered at pharmacological doses, but also is important in normal immune responses. As a consequence, glucocorticoids are widely used as drugs to treat chronic (unnecessarily persistent) inflammatory conditions such as arthritis, nephritis, asthma or dermatitis, and as adjunction therapy for conditions such as autoimmune diseases.

Some of the steroid drugs for topical administration for anti-inflammatory purposes include Betamethasone (Diprolene® cream), Clobetasol (Temovate®, Desonide (Desowen®), Fluocinolone (Derma-Smoothe/FS®), Fluocinonide (Lidex®), Hydrocortisone (Anusol®, Cortaid®, Hydrocortone®), Mometasone (Elocon®) and Triamcinolone (Aristocort®, Knalog®). It is currently believed that the anti-inflammatory properties of glucocorticoids are due to their ability to regulate pro-inflammatory genes, or modulate cellular apoptosis.

There are many drawbacks with the use of steroid drugs which the present invention seeks to address. For example a particular advantage of the administration of 5α reduced glucocorticoid metabolites as opposed to the parent glucocorticoid is that 5α reduced steroids are rapidly conjugated to glucuronides and sulphates in the liver and hence are cleared rapidly from the systemic circulation. These conjugates are inert and are rapidly cleared from the system in the urine. In this regard it is important to consider that no known pathway exists to convert 5α-reduced glucocorticoids into their parent glucocorticoid hormone.

The property of the 5α reduced metabolites having a highly effective first pass conjugation facilitates tissue specific administration of metabolites. For instance, administration of 5α reduced glucocorticoid metabolites to skin (for example by topical administration), lung (for example by intra-articular injection), or liver (for example by mouth) with highly effective first pass conjugation will target 5α reduced glucocorticoid metabolism to the desired tissues while limiting systemic glucocorticoid side effects. Such glucocorticoid mediated side effects include suppression of the HPA axis, osteopenia and osteoporosis, immunocompromise, mood disturbance and insomnia, and adverse metabolic (hyperglycaemia, hyperlipidaemia, obesity) and cardiovascular (hypertension, fluid retention) effects.

Tissue specific modulation of 5α reduced metabolite functional activity may also be achieved utilising the tissue specific distribution of 3α-HSD (Jin & Penning, 2001) (an enzyme involved in 5α reduced metabolite metabolism). Thus activation of 5α-tetrahydrometabolites may be achieved in a tissue specific manner, therefore minimising side effects which are associated with glucocorticoid treatment as detailed above.

The 5α metabolites of the present invention will find particular use when the localised modulation of 5α reduced glucocorticoid functional activity is required. In particular localised increases of 5α reduced metabolite functional activity may be used in the prophylaxis or treatment of inflammatory conditions with reduced side effects as compared with parent glucocorticoid treatment of inflammation. Furthermore, localised decreases of the functional activity of 5α reduced metabolites will be effective in the treatment of obesity, insulin resistance, polycystic ovary syndrome, diabetes mellitus, skin disorders (for hirsutism, acne) cognitive impairment and glucocorticoid-associated mood disturbance with reduced side effects as compared with the treatment of these conditions using the parent glucocorticoid.

It is also contemplated according to the present invention that 5α reduced metabolites may be introduced into sites where they are not normally expressed (ectopic administration). For example, such introduction/administration may have local inflammatory and/or angiostatic effects. Such delivery of 5α reduced metabolites may be performed for example using gene therapy or using liposmes for delivery to macrophages. Those skilled in the art will be aware of other suitable methods for the ectopic administration of reduced metabolites according to the invention herein described.

One skilled in the art will appreciate that the ability to produce tissue specific modulation and/or localised modulation of 5α reduced metabolites permits the operation of multiple modulation strategy (for example, increases in some tissues and decreases in other tissues). This will be of particular use in multiple or complex effect disorders.

In a further aspect the present invention provides a method for modulating angiogenesis within a population of cells comprising the step of modulating the functional activity of one or more 5α-reduced metabolites according to the invention within that population of cells.

In a further aspect still the invention provides the use of one or more modulators of the functional activity of one or more 5α-reduced metabolites in the preparation of a medicament for modulating angiogenesis within a population of cells.

As used herein, the term 'angiogenesis' refers to the formation of blood vessels from surrounding cells. This may occur during for example tissue repair and/or during the invasive growth of tumours. According to the above aspect of the invention, the term 'modulation of angiogenesis' refers to either increasing or decreasing the number of vessels generated during the angiogenesis process as compared with the number of vessels produced in suitable controls. The term the 'modulation of angiogenesis' as defined herein also includes within its scope any alteration in the pattern of vessel formation in the presence of an angiogenesis modulating agent or procedure as herein described. Advantageously the 'modulation of angiogenesis' according to the above aspects of the invention is an inhibition of angiogenesis. Most advantageously as described herein the modulation of angiogenesis is achieved by the use of a modulating agent.

Modulators of the functional activity, as herein defined of one or more 5α-reduced metabolites as defined herein may activate the functional activity or inhibit the functional activity of the one or more 5α-reduced metabolites. In a preferred embodiment of the above aspects of the invention the one or more modulators of the functional activity of the one or more 5α-reduced metabolites are activators of the functional activity of the one or more 5α-reduced metabolites and the modulation of angiogenesis as defined herein involves the inhibition of angiogenesis.

According to the present invention, the modulation of angiogenesis using modulators of the functional activity of one or more 5α-reduced metabolites according to the invention may occur in vivo or in vitro. In a preferred embodiment of the above aspects of the invention the modulation occurs in vivo.

Several studies have suggested that glucocorticoids play a role in the modulation of angiogenesis; Folkman et al (1983). Science, August 19; 221 (4612); 719-25; J Ingber D E, Annals of Surgery (1987); 2-6 (3); 374-383; Jung S P et al (2001); 4 (3); 175-86. Further studies have indicated that glucocorticoids may be used to treat haemangiomas (Hasan et al. (2000). Pediatrics, Jan; 105 (1Pt 1); 117-20. Other studies provide evidence that glucocorticoids may be used in the inhibition of vascular restenosis after intraluminal unjury, a process which is proposed to be amplified by angiogenesis in vasa vasorum (Immunosuppressive therapy for the prevention of restenosis after coronory artery stent implantation; Versaci, F et al (2002), Study. J. Am Coll. Cardiol. December 4; 40 (11); 1935-42. Moreover, the inventors have recently shown that regeneration of corticosterone from 11dehydro-corticosterone within the blood vessel wall by the enzyme 11β-hydroxysteroid dehydrogenase type 1 (11HSD1) is necessary for 11-dehydrocorticosterone to exert an angiostatic effect, which is prevented by antagonism of 11HSD1 or by antagonism of glucocorticoid receptors with RU38486.

The inventors consider that the 5αreduced metabolites according to the invention mimic the action of endogenous glucocorticoids (including those regenerated by 11HSD1) in the activation of glucocorticoid receptors. Thus the inventors consider that 5α-reduced metabolites according to the invention may replace the use of glucocorticoids in the applications described above.

Thus, the present inventors consider that the modulation of angiogenesis using 5αreduced metabolites and/or agents which modulate the functional activity or one or more 5α-reduced metabolites according to the present invention will find use in the prophylaxis and/or treatment of many and varied conditions including any of those selected from the group consisting of: wound healing, vascular restenosis after injury, cancer and tumour growth, collateral circulation after ischaemia or infarction, stroke, diabetic retinopathy, haemangiomas, follicular rupture in ovaries, and endometrial hyperplasia with or without menorrhagia. Those skilled in the art will appreciate that this list is not intended to be exhaustive.

Those skilled in the art will appreciate that the methods of administration of 5α-reduced metabolites and/or agents and/or procedures which modulate their functional activity and the therapeutic strategies described herein, apply equally to the modulation of angiogenesis as to the other therapeutic roles of 5α-reduced metabolites described herein.

The inventors consider that when the inhibition of angiogenesis is required within a population of cells, then advantageously the functional activity of one or more 5α-reduced metabolites within that cell population is inhibited. More advantageously, these methods comprise one or more of the following steps: increasing the levels of one or more 5α-reduced metabolite/s within or near one or more vessels comprising the population of cells; increasing the levels of substrates which are capable of being converted to 5α-reduced metabolites within or near one or more vessels comprising the population of cells and increasing the functional activity of one or more enzymes which increase the functional activity of 5α-reduced metabolites within or near one or more vessels comprising the population of cells (in particular activating or increasing the levels of 3α-hydroxysteroid dehydrogenase and/or 5α-reductase protein).

Suitable methods for the administration of agents which modulate the functional activity of 5α-reduced metabolites as herein defined and/or 5α-reduced metabolites to sites within or near vessels will be known to those skilled in the art. Particularly advantageous methods of administration of such molecules include any one or more of the following: topical administration to vessels via intraluminal or extraluminal routes. In particular, such intraluminal topical administration comprises embolisation or infusion and/or incorporation in a stent. Advantageously, such extraluminal topical administration comprises a gel collar or other local preparation.

The invention will now be further described by way of the following non-limiting examples.

Example 1

Binding of Glucocorticoid Metabolites to Glucocorticoid Receptor

Figure 1:
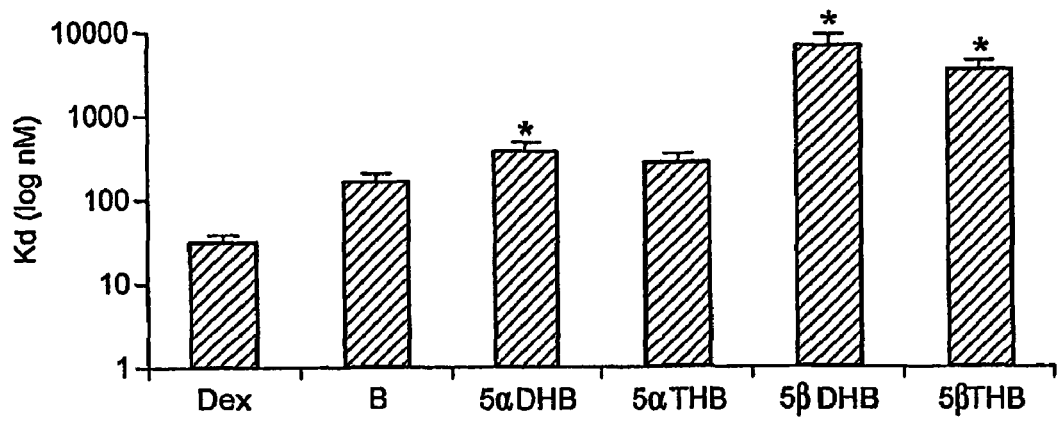
FIG. 1 shows the binding of glucocorticoid metabolites to the glucocorticoid receptor.

Data shows that 5α-tetrahydrocorticosterone (5αTHB) has an equivalent binding affinity for glucocorticoid receptors (GR) in hepatocytes as corticosterone (B) ($p>0.05$), whereas 5α-dihydrocorticosterone (5αDHB) and 5β-reduced metabolites have lower binding affinities ($p<0.05$). Hepatocytes were incubated at 24° C. for 1 h in the presence of $^3$H-dexamethasone and increasing concentrations of dexamethasone in the concentration range 0.632 nM to 200 µM. Cells were harvested and the radioactivity bound was determined by β-scintillation counting. *=$p<0.001$ versus B. The results are shown in FIG. 1.

Example 2

Figure 2:
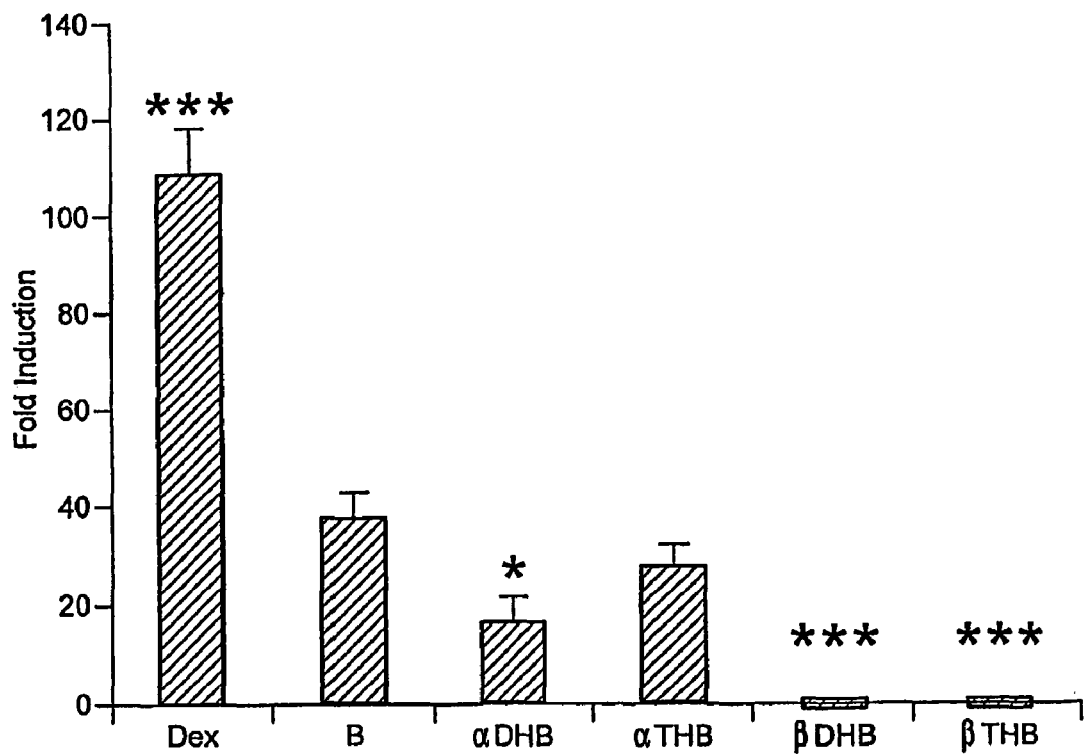
FIG. 2 shows transfection experiments to demonstrate glucocorticoid receptor activation of gene transcription by 5α-reduced glucocorticoid metabolites. Comparative potency Fold induction of luciferase activity as a consequence of GR activation in Hela cells transfected with GR and luciferase under the control of a GRE and MMTV promoter (n=3). All steroids at 1 µM. Dex=dexamethasone; B=corticosterone; αDHB=5α-dihydrocorticosterone; αTHB=5α-tetrahydrocorticosterone; βDHB=5β-dihydrocorticosterone; βTHB=5β-tetrahydrocorticosterone. *indicates $p<0.05$ and ***$p<0.001$ in comparison with corticosterone. 5α-reduced metabolites of corticosterone activate glucocorticoid receptors with similar potency as corticosterone. 5α-tetrahydrocorticosterone is more potent than 5α-dihydrocorticosterone. 5β-reduced metabolites have no effect.

Transfection Experiments to Show Glucocorticoid Receptor Activation of Gene Transcription by 5α-Reduced Glucocorticoid Metabolites Comparative potency Fold induction of luciferase activity as a consequence of GR activation in Hela cells transfected with GR and luciferase under the control of a GRE and MMTV promoter (n=3). All steroids at 1 µM. Dex=dexamethasone; B=corticosterone; αDHB=5α-dihydrocorticosterone; αTHB=5α-tetrahydrocorticosterone; βDHB=5β-dihydrocorticosterone; βTHB=5β-tetrahydrocorticosterone. *indicates $p<0.05$ and ***$p<0.001$ in comparison with corticosterone. 5α-reduced metabolites of corticosterone activate glucocorticoid receptors with similar potency as corticosterone (B). 5α-tetrahydrocorticosterone is more potent than 5α-dihydrocorticosterone. 5β-reduced metabolites have no effect. The results are shown in FIG. 2.

Figure 3:
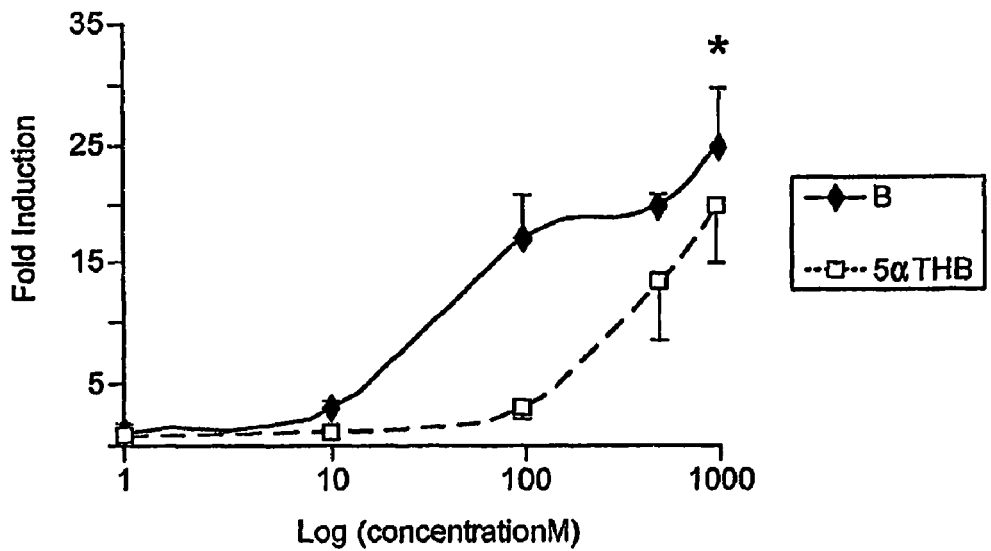
FIG. 3 shows transfection experiments to demonstrate glucocorticoid receptor activation of gene transcription by 5α-reduced glucocorticoid metabolites.

Dose response. Fold induction of luciferase activity as a consequence of GR activation in Hela cells transfected with GR and luciferase under the control of a GRE and MMTV promoter (n=3). Both steroids activate a glucocorticoid receptor-dependent response. Statistical analysis by Repeated measure ANOVA shows a significant difference (p<0.05) in the potency of the two steroids to activate GR, with 5α-tetrahydrocorticosterone (5α-THB) having a lesser effect than corticosterone (B). The results are shown in FIG. 3.

Example 3

The Dependence of Glucocorticoid Receptor Activation by 5Alpha-Reduced Glucocorticoid Metabolites on the Presence of the Glucocorticoid Receptor The results are shown in FIG. 4.

FIG. 4 shows luciferase induction in response to glucocorticoid activation of the glucocorticoid receptor (GR). Corticosterone (B) and 5α-tetrahydrocorticosterone (5αTHB) or vehicle (LTR) were added to the medium (with final steroid concentrations of 1 micromol/l) of Hela cells transfected with GR and a plasmid expressing luciferase under the control of an MMTV glucocorticoid responsive promoter (grey bars) and in transfected cells with luciferase but without GR (open bars). Both steroids activated GR and these responses were abolished in the absence of transfected receptor.

Example 4

Full Agonist Rather than Partial Agonist Activity of 5Alpha-Tetrahydrocorticosterone on Glucocorticoid Receptors The results are shown in FIG. 5.

HeLa cells were transfected with glucocorticoid receptor (GR) and MMTV-luciferase (LTR) as a glucocorticoid sensitive reporter. Induction of luciferase was measured in response to addition of 5α-tetrahydrocorticosterone (5α-THB) with and without corticosterone (B). Data (mean±SEM, n=6) show responses to individual steroids, then the additive responses predicted (Sum) and observed (Actual). The lack of difference between observed and predicted indicates that 5alpha-THB is a full rather than partial agonist of GR.

Example 5

5Alpha-Reduced Metabolites of the Human Glucocorticoid, Cortisol, also Activate Glucocorticoid Receptors The results are shown in FIG. 6.

HeLa cells were transfected with glucocorticoid receptor (GR) and MMTV-luciferase (LTR) as a glucocorticoid sensitive reporter. Induction of luciferase was measured in response to addition of 1 micromol/l concentrations of corticosterone (B), cortisol (F), 5alpha-dihydrocortisol (DHF5a) and 5alpha-tetrahydrocortisol (THF5a). All of these steroid induced significant GR activation.

Example 6

5Alpha-Reduced Glucocorticoid Metabolites are Glucocorticoid Receptor (GR) Agonists in Cells which Express Endogenous Glucocorticoid Receptors The results are shown in FIG. 7.

Induction of the glucocorticoid-responsive enzyme tyrosine amino transferase (TAT) mRNA was measured by Northern blot in H4iiE cells incubated in the presence of corticosterone (B, 1 micromol/l) or 5α-tetrahydrocorticosterone (5α-THB, 1 micromol/l) or vehicle. Both steroids induced TAT mRNA transcription (determined by Northern Blot, corrected for U1) and this was blocked by a glucocorticoid receptor antagonist, RU486 (present for open bars only).

Example 7

5Alpha-Tetrahydrocorticosterone is a Glucocorticoid Receptor Agonist In Vivo

The results are shown in FIG. 8.

Male lean Zucker rats aged ~9 weeks were adrenalectomised. 3 weeks later, samples were obtained by tail tipping before and for 3 hours after intraperitoneal injection of either vehicle, corticosterone (B, 5 mg/kg body weight) or 5alpha-tetrahydrocorticosterone (THB5a, 5 mg/kg body weight). By comparison with vehicle, at 2 hours after injection, both corticosterone and 5α-tetrahydrocorticosterone had significantly suppressed ACTH levels, measured by immunoassay. This is consistent with activation of glucocorticoid receptors at sites responsible for feedback suppression of the hypothalamic-pituitary-adrenal axis (principally pituitary, hypothalamus and hippocampus).

Example 8

5Alpha Reduced Metabolites Inhibit Angiogenesis in Vascular Tissue

The results are shown in FIG. 9. Specifically FIG. 9 shows that 5alpha-tetrahydrocorticosterone is a glucocorticoid receptor agonist in intact isolated tissue preparations.

In this bioassay, the number of new vessels forming is measured over 7 days in a mouse aortic ring embedded in matrigel. As shown here, corticosterone (B, 600 nmol/l) inhibits angiogenesis compared with vehicle (veh) and this is blocked by the glucocorticoid receptor (GR) antagonist RU486. 5alpha-tetrahydrocorticosterone (5alpha-THB, 1000 nmol/l) also prevents angiogenesis and this is also blocked by RU486. RU486 has no effect on its own.

REFERENCES

Andrew, R., Phillips, D. I. W., & Walker, B. R. (1998) Obesity and gender influence cortisol secretion and metabolism in man. *Journal of Clinical Endocrinology and Metabolism* 83, 1806-1809.

Bamberger, C. M., Schulte, H. M., and Chrousos, G. P. Molecular determinants of glucocorticoid receptor function and tissue sensitivity to glucocorticoids. Endocrine Reviews 17, 245-261. 1996.

Bartsch, G., Rittmaster, R. S., & Klocker, H. (2000) Dihydrotestosterone and the concept of 5α-reductase inhibition in human benign prostatic hyperplasia. *European Urology* 37, 367-387.

Carlstedt-Duke, J., Gustafsson, J. A., Gustafsson, S. A., & Wrange, O. (1977) Interactions of corticosterone, 5alpha-corticosterone and dexamethasone with proteins in rat-liver cytosol. *European Journal of Biochemistry* 73, 231-238.

Dubrovsky, B. O., Liquomik, M. S., Noble, P., & Gijsbers, K. (1987) Effects of 5α-dihydrocorticosterone on evoked responses and long-term potentiation. *Brain Research Bulletin* 19, 635-638.

Edwards, C. R. W., Stewart, P. M., Burt, D., Brett, L., McIntyre, M. A., Sutanto, W. S., DeKloet, E. R., & Monder, C. (1988) Localisation of 11β-hydroxysteroid dehydrogenase-tissue specific protector of the mineralocorticoid receptor. *Lancet* ii, 986-989.

Funder, J. W., Pearce, P. T., Smith, R., & Smith, A. I. (1988) Mineralocorticoid action: target tissue specificity is enzyme, not receptor, mediated. *Science* 242, 583-585.

Golf, S. W., Bepperling, F., & Graef, V. (1984) Effect of 5α-dihydrocorticoids on enzymes of gluconeogenesis in rat liver. *Steroids* 43, 85-91.

Guarna, A., Occhiato, E. G., Danza, G., & et al (1998) 5α-Reductase inhibitors, chemical and clinical models. *Steroids* 63, 355-361.

Hirsch, K. S., Jones, C. D., Audia, J. E., Andersson, S., McQuaid, L., Stamm, N. B., Neubauer, B. L., Pennington, P., Toomey, R. E., & Russell, D. W. (1993) LY191704: A selective, nonsteroidal inhibitor of human steroid 5alpha-reductase type. *Proceedings of the National Academy of Sciences of the United States of America* 90, 5277-5281.

Jin, Y. & Penning, T. M. (2001) Steroid 5[alpha]-reductases and 3[alpha]-hydroxysteroid dehydrogenases: key enzymes in androgen metabolism. *Bailliere's Best Practice and Research in Clinical Endocrinology and Metabolism* 15, 79-94.

Kotelevtsev, Y. V., Holmes, M. C., Burchell, A., Houston, P. M., Scholl, D., Jamieson, P. M., Best, R., Brown, R. W., Edwards, C. R. W., Seckl, J. R., & Mullins, J. J. (1997) 11β-Hydroxysteroid dehydrogenase type 1 knockout mice show attenuated glucocorticoid inducible responses and resist hyperglycaemia on obesity and stress. *Proceedings of the National Academy of Sciences USA* 94, 14924-14929.

Lackner, C., Davani, B., Wildt, L., & Allera, A. (1998) Glucocorticoid-recognizing and -effector sites in rat liver plasma membrane. Kinetics of corticosterone uptake by isolated membrane vesicles. III. Specificity and stereospecificity. *Journal of Steroid Biochemistry & Molecular Biology* 64, 69-82.

Livingstone, D. E. W., Jones, G. C., Smith, K., Andrew, R., Kenyon, C. J., & Walker, B. R. (2000) Understanding the role of glucocorticoids in obesity: tissue-specific alterations of corticosterone metabolism in obese Zucker rats. *Endocrinology* 141, 560-563.

Lopez-Guerra, A., Chirino, R., Navarro, D., Fernandez, L., & Navarro, D. (1997) Estrogen antagonism on T3 and growth hormone control of the liver microsomal low-affinity glucocorticoid binding site (LAGS). *Journal of Steroid Biochemistry & Molecular Biology* 63, 219-228.

Masuzaki, H., Paterson, J., Shinyama, H., Morton, N. M., Mullins, J. J., Seckl, J. R., & Flier, J. S. (2001) A Transgenic Model of Visceral Obesity and the Metabolic Syndrome. *Science* 294, 2166-2170.

Phillipou, G. (1982) Investigation of urinary steroid profiles as a diagnostic method in Cushing's syndrome. *Clinical Endocrinology (Oxford)* 16, 433-439.

Russell, D. W. & Wilson, J. D. (1994) Steroid 5α-reductase: two genes/two enzymes. *Annual Reviews of Biochemistry* 63, 25-61.

Seckl, J. R. & Walker, B. R. (2001) 11β-Hydroxysteroid dehydrogenase type 1—a tissue-specific amplifier of glucocorticoid action. *Endocrinology* 142, 1371-1376.

Soro, A., Ingram, M. C., Tonolo, G., Glorioso, N., & Fraser, R. (1995) Evidence of coexisting changes in 11β-hydroxysteroid dehydrogenase and 5β-reductase activity in patients with untreated essential hypertension. *Hypertension* 25, 67-70.

Steckelbroeck, S., Watzka, M., Reichelt, R., Hans, V. H. J., & Stoffel-Wagner, B. (2001) Characterization of the 5[alpha]-reductase-3[alpha]-hydroxysteroid dehydrogenase complex in the human brain. *Journal of Clinical Endocrinology & Metabolism* 86, 1324-1331.

Stewart, P. M. & Krozowski, Z. S. (1999) 11Beta hydroxysteroid dehydrogenase. *Vitamins and Hormones* 57, 249-324.

Stewart, P. M., Shackleton, C. H. L., Beastall, G. H., & Edwards, C. R. W. (1990) 5alpha-reductase activity in polycystic ovarian syndrome. *Lancet* 335, 431-433.

Stewart, P. M. & Sheppard, M. C. (1992) Novel aspects of hormone action: intracellular ligand supply and its control by a series of tissue specific enzymes. *Molecular and Cellular Endocrinology* 83, C13-18.

Walker, B. R., Connacher, A. A., Lindsay, R. M., Webb, D. J., & Edwards, C. R. W. (1995) Carbenoxolone increases hepatic insulin sensitivity in man: a novel role for 11-oxosteroid reductase in enhancing glucocorticoid receptor activation. *Journal of Clinical Endocrinology and Metabolism* 80, 3155-3159.

Walker, B. R., Phillips, D. I. W., Noon, J. P., Panarelli, M., Best, R., Edwards, H. E., Holton, D. W., Seckl, J. R., Webb, D. J., & Watt, G. C. M. (1998) Increased glucocorticoid activity in men with cardiovascular risk factors. *Hypertension* 31, 891-895.

The invention is further described by the following numbered paragraphs:

(1) A method for modulating the activation of one or more glucocorticoid receptors comprising the step of modulating the functional activity of one or more 5α reduced metabolite/s capable of binding to the one or more receptor/s.

(2) A method for modulating the functional activity of one or more glucocorticoid receptors comprising the step of modulating the functional activity of one or more 5α reduced metabolite/s capable of binding to the one or more receptor/s.

(3) A method according to paragraph 1 or paragraph 2 wherein the functional activity of one or more 5 cc reduced metabolites is modulated using at least one agent selected from the group consisting of: finasteride, G1108745, indomethacin and LY191704.

(4) A method for inhibiting one or more glucocorticoid mediated effects in one or more tissues of a patient, those effects being selected from the group consisting of the following: in liver (glucocorticoid-dependent promotion of gluconeogenesis in liver, resistance to insulin in liver, intra-hepatic fat accumulation, non-alcoholic steatohepatitis in liver and cirrhosis of the liver, and hyperlipidaemia), adipose (glucocorticoid-dependent increase in lipid accumulation, resistance to insulin, and inhibition of glucose uptake), brain (glucocorticoid-associated cognitive decline and mood disturbance) and skin (preventing glucocorticoid-induced skin thinning, bruising, hirsutism, and acne) comprising the step of inhibiting the functional activity of one or more 5a reduced metabolite/s capable of binding to the one or more receptor/s.

(5) A method for inhibiting one or more glucocorticoid mediated effects or conditions according to paragraph 4 wherein the effect or condition is one or more of those selected from the group consisting of: obesity, insulin resistance, polycystic ovary syndrome, diabetes mellitus, skin disorders (hirsutism, acne) cognitive impairment, and glucocorticoid-associated mood disturbance.

(6) A method for inhibiting one or more glucocorticoid mediated effects or conditions according to paragraph 4 or paragraph 5 wherein the functional activity of one or more 5α reduced metabolite/s capable of binding to the one or more receptor/s is inhibited using an agent selected from the group consisting of the following: finasteride, GI198745, indomethacin and LY191704.

(7) A method for the treatment of one or more inflammatory conditions in a patient comprising the step of increasing the functional activity of one or more 5α reduced metabolite/s in the one or more sites of inflammation of a patient.

(8) A method according to paragraph 7 wherein the functional activity of one or more 5α reduced glucocorticoid metabolites is increased by any of the procedures selected from the group consisting of: administering to a patient in need of such treatment a therapeutically effective amount of one or more 5α reduced metabolite/s, increasing 5α reductase activity, reducing pathways of inactivation of cortisol, reducing the conjugation of 5α reduced metabolites and effecting the conversion of 5α-dihydro reduced metabolite compounds to 5α-tetrahydro reduced metabolite compounds.

(9) A method according to paragraph 8 wherein the functional activity of one or more 5α reduced glucocorticoid metabolites is increased by administering to a patient in need of such treatment a therapeutically effective amount of one or more 5α reduced metabolite/s.

(10) A method according to any preceding paragraph wherein at least one 5α reduced metabolite is selected from the group consisting of: 5α-dihydrocortisol, 5α-tetrahydrocortisol, 5α-dihydrocorticosterone and 5α-tetrahydrocorticosterone.

(11) A method according to paragraph 10 wherein at least one 5α reduced metabolite is 5α-tetrahydrocorticosterone.

(12) A composition comprising one or more 5α reduced metabolites and a physiologically acceptable carrier diluent or exipient.

(13) A composition according to paragraph 12 comprising one or more 5α reduced metabolites selected from the group consisting of: 5α-dihydrocortisol, 5α-tetrahydrocortisol, 5α-dihydrocorticosterone and 5α-tetrahydrocorticosterone.

(14) The use of one or more modulator/s of the functional activity of one or more 5α reduced metabolites in the preparation of a medicament for modulating the activation of one or more glucocorticoid receptor/s.

(15) The use of one or more modulator/s of the functional activity of one or more 5α reduced metabolites in the preparation of a medicament for modulating the functional activity of one or more glucocorticoid receptors.

(16) The use according to paragraph 14 or paragraph 15 wherein at least one modulator is an agent selected from the group consisting of: finasteride, GI108745, indomethacin and LY191704.

(17) The use of one or more inhibitors of the functional activity of one or more 5α reduced metabolites in the preparation of a medicament for the prophylaxis or treatment of a condition selected from the group consisting of the following: glucocorticoid-dependent promotion of in liver (gluconeogenesis in liver, resistance to insulin in liver, intra-hepatic fat accumulation, non-alcoholic steatohepatitis in liver and cirrhosis of the liver, and hyperlipidaemia), adipose (glucocorticoid-dependent increase in lipid accumulation, resistance to insulin, and inhibition of glucose uptake), brain (glucocorticoid-associated cognitive decline and mood disturbance) and skin (preventing glucocorticoid-induced skin thinning, bruising, hirsutism, and acne).

(18) The use according to paragraph 17 wherein at least one inhibitor is an agent selected from the group consisting of: finasteride, GI198745, LY191704, G1108745 and indomethacin.

(19) The use of one or more activator/s of the functional activity of one or more 5α reduced metabolite/s in the preparation of a medicament for the prophylaxis or treatment of one or more inflammatory conditions in a patient.

(20) The use of according to paragraph 19 wherein at least one activator of 5α reduced metabolite functional activity is a 5α reduced glucocorticoid metabolite.

(21) The use according to any one of paragraphs 19 or paragraph 20 wherein one or more 5α reduced metabolites are selected from the group consisting of: 5α-dihydrocortisol, 5α-tetrahydrocortisol, 5α-dihydrocorticosterone and 5α-tetrahydrocorticosterone.

(22) The use according to paragraph 21 wherein at least one 5α reduced metabolite is 5α-tetrahydrocorticosterone.

(23) A method for modulating angiogenesis within a population of cells comprising the step of modulating the functional activity of one or more 5α reduced metabolites according to paragraph 21 within that population of cells.

(24) The use of one or more modulators of the functional activity of one or more 5α reduced metabolites in the preparation of a medicament for modulating angiogenesis within a population of cells.

(25) The use according to paragraph 24 wherein the one or more 5α reduced metabolites comprises any one or more of those listed in paragraph 21.

(26) A method or a use according to any of paragraphs 23 to 25 wherein the modulator of the functional activity of 5α reduced metabolites is an activator of the functional activity of the metabolite.

(27) A method or a use according to paragraph 26 wherein the functional activity of the metabolite is activated using one or more of the following steps: increasing the levels of one or more 5α-reduced metabolite/s within or near one or more vessels comprising the population of cells; increasing the levels of substrates which are capable of being converted to 5α-reduced metabolites within or near one or more vessels comprising the population of cells; activating or increasing the levels of 3α-hydroxysteroid dehydrogenase and/or 5α-reductase protein within or near one or more vessels comprising the population of cells.

(28) A method or a use according to any of paragraphs 23 to 27 wherein angiogenesis is inhibited.

(29) A method or a use according to paragraph 28 wherein the inhibition of angiogenesis within a population of cells occurs in vivo.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular biology and biotechnology or related fields are intended to be within the scope of the following claims.

What is claimed is:

1. A method for the treatment of one or more inflammatory conditions in a patient consisting essentially of the step of increasing the functional activity of one or more 5α reduced glucocorticoid metabolite/s in the one or more sites of inflammation of a patient by administering to a patient in need of such treatment a therapeutically effective amount of a composition consisting of one or more 5α reduced glucocorticoid metabolite/s as active ingredient/s and a physiologically acceptable carrier, diluent or excipient, such that the functional activity of one or more 5α reduced glucocorticoid metabolite/s in the one or more sites of inflammation is increased.

2. The method according to claim 1, wherein at least one 5α reduced glucocorticoid metabolite is selected from the group consisting of: 5α-dihydrocortisol, 5α-tetrahydrocortisol, 5α-dihydrocorticosterone and 5α-tetrahydrocorticosterone.

3. The method according to claim 1, wherein at least one 5α reduced metabolite is 5α-dihydrocortisol.

4. The method according to claim 1, wherein at least one 5α reduced glucocorticoid metabolite is 5α-tetrahydrocortisol.

5. The method according to claim 1, wherein at least one 5α reduced glucocorticoid metabolite is 5α-dihydrocorticosterone.

6. The method according to claim 1, wherein at least one 5α reduced glucocorticoid metabolite is 5α-tetrahydrocorticosterone.

* * * * *